United States Patent
Gilham et al.

(10) Patent No.: US 11,639,496 B2
(45) Date of Patent: May 2, 2023

(54) REDUCING FRATRICIDE OF IMMUNE CELLS EXPRESSING NKG2D-BASED RECEPTORS

(71) Applicant: CELYAD S.A, Mont-Saint-Guibert (BE)

(72) Inventors: David Gilham, Mont-Saint-Guibert (BE); Eytan Breman, Mont-Saint-Guibert (BE); Benjamin Demoulin, Mont-Saint-Guibert (BE); Simon Bornschein, Mont-Saint-Guibert (BE); Susanna Raitano, Mont-Saint-Guibert (BE)

(73) Assignee: CELYAD S.A., Mont-Saint-Guibert (BE)

( * ) Notice: Subject to any disclaimer, the term of this patent is extended or adjusted under 35 U.S.C. 154(b) by 282 days.

(21) Appl. No.: 16/769,627

(22) PCT Filed: Dec. 5, 2018

(86) PCT No.: PCT/EP2018/083661
§ 371 (c)(1),
(2) Date: Jun. 4, 2020

(87) PCT Pub. No.: WO2019/110667
PCT Pub. Date: Jun. 13, 2019

(65) Prior Publication Data
US 2020/0318067 A1     Oct. 8, 2020

(30) Foreign Application Priority Data
Dec. 5, 2017 (EP) ..................... 17205560

(51) Int. Cl.
*C12N 5/00* (2006.01)
*C12N 5/0783* (2010.01)
*A61P 35/00* (2006.01)
*A61K 35/17* (2015.01)
*C12N 15/113* (2010.01)

(52) U.S. Cl.
CPC ............ *C12N 5/0636* (2013.01); *A61K 35/17* (2013.01); *A61P 35/00* (2018.01); *C12N 15/1138* (2013.01); *C12N 2310/14* (2013.01); *C12N 2310/531* (2013.01); *C12N 2510/00* (2013.01)

(58) Field of Classification Search
CPC ............ C12N 5/0636; C12N 15/1138; C12N 2310/14; C12N 2310/531; C12N 2510/00; C12N 2310/20; C12N 2310/3233; C12N 2501/727; C12N 2501/998; A61K 35/17; A61K 38/177; A61P 35/00; C07K 14/7056
See application file for complete search history.

(56) References Cited

U.S. PATENT DOCUMENTS

2007/0248607 A1 * 10/2007 Spies ................. A61P 1/04
435/7.1
2012/0029063 A1   2/2012 Zhang et al.
2017/0218337 A1   8/2017 Friedman

FOREIGN PATENT DOCUMENTS

WO   WO 2005/097160   * 10/2005 ............. A61K 38/00
WO         2014117121     7/2014

OTHER PUBLICATIONS

Sadelain et al. (Cancer Discovery, 388-398, 2013).*

* cited by examiner

*Primary Examiner* — Nelson B Moseley, II
(74) *Attorney, Agent, or Firm* — Robin L. Teskin; Baker, Donelson, Bearman, Caldwell & Berkowitz PC

(57) ABSTRACT

The present application relates to the field of immunotherapy, more particularly to the manufacture of cells for adoptive cell therapy. Provided herein are methods to prevent and/or reduce fratricide during manufacturing of such cells, particularly of cells expressing a chimeric NKG2D receptor. Also provided are cells and compositions comprising cells in which fratricide is prevented and/or reduced.

18 Claims, 15 Drawing Sheets

E

F

| | Name | MFI : CD314 | Vector copy number |
|---|---|---|---|
| | NKR-2 | 267 | 1,86 |
| | NKR-2 + LY 1 µM | 237 | 2,03 |
| | NKR-2 + LY 5 µM | 179 | 2,58 |
| | NKR-2 + LY 10µM | 79,2 | 2,48 |

A

B

A

B

C

REDUCING FRATRICIDE OF IMMUNE CELLS EXPRESSING NKG2D-BASED RECEPTORS

CROSS-REFERENCE TO RELATED APPLICATIONS

This application is a U.S. National Phase Application of Intl Appl. No. PCT/EP2018/083661, filed Dec. 5, 2018, which claims priority to Intl Appl. No. EP 17205560.0, filed Dec. 5, 2017, each of which is incorporated herein by reference.

FIELD OF THE INVENTION

The present application relates to the field of immunotherapy, more particularly to the manufacture of cells for adoptive cell therapy. Provided herein are methods to prevent and/or reduce fratricide during manufacturing of such cells, particularly of cells expressing a chimeric NKG2D receptor. Also provided are cells and compositions comprising cells in which fratricide is prevented and/or reduced.

BACKGROUND

Improvements in our understanding of the immune system have led to the development of many immune focused therapies that are now delivering objective clinical responses in patients with advanced cancer. One of these approaches is the Chimeric Antigen Receptor (CAR) T cell where patients' T cells are gene-modified to express a tumor targeting CAR and then returned to the patient in large numbers(1). This adoptive cell therapy has achieved a level of validation through objective clinical responses in patients with hematological malignancies and is being further explored for the therapy of broader cancer indications(2-7). The CAR concept is also moving beyond T cells with CARs being explored in a range of cell types including Natural Killer cells(8).

CARs are modular protein receptors that consist of a target binding domain linked to structural domains that generally include an extracellular spacer domain and a transmembrane region fused to intracellular signaling domains. Upon ligand binding, downstream signaling initiated from the CAR activates the effector function of the T cell thereby driving direct tumor cell killing and immune-recruiting cytokine production.

A common issue to CAR T production is self-killing (or fratricide). This phenomenon occurs when the CAR target is expressed on the T cell population. T cell fratricide is well understood as a mechanism to maintain T cell homeostasis (13); however, in the therapeutic setting, T cell fratricide prevents the ability to produce the desired CAR T cell population for clinical application. This is particularly pertinent in the situation where the target itself is chosen for T cell lineage specificity such as CD7(14) or CD5(15) to enable targeting of T cell leukemias. However, the issue is not restricted to CAR T cell therapy. T cells armed with high affinity TCR for T cell receptors specific for survivin (BIRC5) undergo fratricide due to expression of the target antigen(16, 17). Likewise, NK cells expressing ligands of NK receptors have also shown to be suffering from fratricide (24).

In conclusion, endowing immune cells (e.g. T or NK cells) with a pre-defined target specificity by means of an artificial cell surface chimeric antigen receptor (CAR) construct provides an approach to putatively target any tumor cell. The success of the approach is largely dependent upon the profile of the target antigen itself where most known tumor antigens are not specific to the tumor but are potentially expressed on non-neoplastic cells. In certain circumstances, the target antigen may be constitutively or transiently expressed on an immune cell meaning that the CAR-modified cell may undergo self-killing or fratricide.

Here, the focus is upon CAR T cells engineered with specificity for stress ligands targeted by the Natural Killer Group 2 D (NKG2D) protein. Fusion of the full length NKG2D sequence with the cytoplasmic domain of CD3ζ generates a CAR construct that upon ligand binding by the NKG2D extracellular domain results in T cell activation through the CD3ζ domain(18). NKG2D has eight known ligands including the major histocompatibility complex class I-related A and B gene (MICA and MICB respectively) and the UL16-binding protein (ULBP) family (ULBP1-6) (19). Expression of these NKG2D ligands is known to be induced under 'stress' conditions such as cellular damage, infection, oxidative or thermal stress, or malignant transformation leading to a broad range of human tumors that express NKG2D ligands underscoring the attractiveness of NKG2D as a receptor to be exploited in the CAR context(19, 20). Indeed, mouse T cells bearing the murine NKG2D CAR effectively eradicate a range of established hematological and solid tumors in syngeneic model systems demonstrating the proof of concept of the approach(18).

Human T cells bearing the human NKG2D CAR (also termed NKR-2) engage effector cell function against a range of tumor cells in vitro and can challenge established human tumor in the NSG mouse model(21). However, the upscaling of NKR-2 cell production to generate higher cell numbers for clinical application proved to be highly problematic with T cell fratricide identified as the cause due to the transient expression of NKG2D ligands by activated T cells.

Thus, a CAR consisting of a fusion of the NKG2D protein with CD3ζ (NKR-2) endows T cells with broad specificity for NKG2D ligands. However, T cells transiently express these ligands during activation and, consequently, NKR-2 T cells undergo fratricide thereby substantially hampering the ability to exploit NKG2D as a therapy. Further, to use a therapy in the clinic, significant upscaling and cryopreservation is needed to deliver the required dosing schedule. Cryopreservation and freeze-thaw cycles are known to be stressful to cells, which leads to increased expression of stress-inducible proteins such as the NKG2D ligands. It was indeed observed that both up-scaling and cryopreservation of chimeric NKG2D receptor-expressing T cells resulted in poor cell yields, presumably due to self-killing or fratricide.

Accordingly, it would be advantageous to prevent or reduce the occurrence of fratricide in these cells, as this would not only increase the yield of the cells, but also decrease the cost of manufacturing and enhance the therapeutic efficacy of these cells—in short, it would make the upscaling and cryopreservation needed for clinical applications feasible from a practical and commercial perspective.

SUMMARY

Modified immune cells, in particular Chimeric Antigen Receptor (CAR) T cells, expressing the fusion of the NKG2D protein with CD3ζ (NKG2D-CAR T Cells) acquire a specificity for stress-induced ligands expressed on hematological and solid cancers. However, these stress ligands are also transiently expressed by activated immune or T cells implying that NKG2D-based immune cells may undergo self-killing (fratricide) during cell manufacturing or during the freeze thaw cycle prior to infusion in patients.

It is an object of the invention to provide methods of reducing and/or preventing fratricide during manufacturing of immune cells expressing a chimeric NKG2D receptor, comprising functional inhibition of NKG2D signaling during the manufacturing process of the cells. It is also an object of the invention to provide methods of reducing and/or preventing fratricide during freezing and/or thawing of frozen immune cells expressing a chimeric NKG2D receptor, comprising functional inhibition of NKG2D signaling during the freezing and/or thawing process of the cells.

By means of targeted inhibition of NKG2D expression, NKG2D ligand expression or inhibition of enzyme function, particularly PI3K function, target-driven CAR T fratricide can be overcome. It is particularly envisaged that functional inhibition of NKG2D signaling can be achieved by one or more of:

Permanent or transient inhibition of one or more of the NKG2D ligands of the immune cells;
Transient inhibition of the chimeric NKG2D receptor;
Transient inhibition of downstream signaling of the chimeric NKG2D receptor.

According to embodiments where permanent inhibition of the one or more of the NKG2D ligands is envisaged, this can particularly be achieved by genetic knockdown. To this end, gene editing techniques including, but not limited to, Crispr/Cas, TALEN, ZFN, meganucleases, MegaTAL nucleases can be used.

According to particular embodiments where transient inhibition of downstream signaling is envisaged, this is transient inhibition of PI3K signaling. According to further particular embodiments, PI3K signaling can be inhibited using a broad range PI3K inhibitor. An example of such an inhibitor is LY294002. Another suitable inhibitor is idelalisib (Cal-101).

According to particular embodiments, functional inhibition of receptor or ligands can be achieved using inhibitory RNA (such as shRNA or siRNA) or an antibody against the NKG2D receptor or against one or more of its ligands.

According to further particular embodiments, functional inhibition is achieved at the receptor level and is done through inhibitory RNA or an antibody against the NKG2D receptor. According to one aspect, an antibody against the NKG2D receptor is used. In particular embodiments of this aspect, the antibody against the NKG2D receptor is an antibody that binds the receptor without activating the chimeric receptor (i.e. a blocking or antagonistic antibody). According to most particular embodiments, the antibody against the NKG2D receptor is the commercially available 1D11 antibody (named after the clone from which it was isolated).

According to alternative particular embodiments, functional inhibition is achieved at the ligand level and is done through inhibitory RNA or an antibody against one or more of the NKG2D ligands. It is particularly envisaged that the ligands are one or both of MICA and MICB. According to one aspect, shRNA against one or more NKG2D ligands is used.

According to particular embodiments, the immune cells to be manufactured are cells for adoptive cell transfer such as T cells, NK cells, NKT cells, stem cells or iPSCs.

In a further aspect, cells are provided that suffer less from fratricide when being manufactured for adoptive transfer. According to this aspect, engineered immune cells are provided comprising a nucleic acid molecule encoding a chimeric NKG2D receptor and at least one of:

One or more endogenous genes encoding a NKG2D ligand that have been engineered to be inactivated;
One or more shRNAs directed against the chimeric NKG2D receptor and/or one or more NKG2D ligands.

In these immune cells, NKG2D ligands are selected from: MICA, MICB, ULBP1, ULBP2, ULBP3, ULBP4, ULBP5 and ULBP6. Particularly envisaged ligands are MICA and/or MICB.

According to further particular embodiments, engineered immune cells are provided comprising a nucleic acid molecule encoding a chimeric NKG2D receptor and at least one of:

One or more endogenous genes encoding a NKG2D ligand that have been engineered to be inactivated;
One or more shRNAs directed against one or more NKG2D ligands.

According to a further aspect, compositions are provided containing immune cells comprising a nucleic acid molecule encoding a chimeric NKG2D receptor and
  a) the cells further comprising
    One or more endogenous genes encoding a NKG2D ligand that have been engineered to be inactivated;
    One or more shRNAs directed against the chimeric NKG2D receptor and/or one or more NKG2D ligands;
    and/or
  b) the composition further comprising
    One or more antibodies directed against the chimeric NKG2D receptor and/or one or more NKG2D ligands;
    An inhibitor of downstream signaling of the chimeric NKG2D receptor, particularly a PI3K inhibitor.

According to particular embodiments of this aspect, compositions are provided containing immune cells comprising a nucleic acid molecule encoding a chimeric NKG2D receptor, the composition further comprising
  One or more antibodies directed against the chimeric NKG2D receptor and/or one or more NKG2D ligands;
  and/or
  An inhibitor of downstream signaling of the chimeric NKG2D receptor, particularly a PI3K inhibitor.

According to yet further particular embodiments, compositions are provided containing immune cells comprising a nucleic acid molecule encoding a chimeric NKG2D receptor, the composition further comprising
  One or more antibodies directed against the chimeric NKG2D receptor; and/or
  A PI3K inhibitor, particularly LY294002 or idelalisib.

According to yet a further aspect, the engineered immune cells or the compositions described herein are provided for use as a medicament. They are particularly suited for use in the treatment of cancer.

This is equivalent as stating that methods of treating cancer are provided, comprising administering an engineered immune cell comprising a nucleic acid molecule encoding a chimeric NKG2D receptor and at least one of:

One or more endogenous genes encoding a NKG2D ligand that have been engineered to be inactivated;
One or more shRNAs directed against the chimeric NKG2D receptor and/or one or more NKG2D ligands.
to a subject in need thereof.

Likewise, methods of treating cancer are provided, comprising administering a composition to a subject in need thereof, wherein the composition contains immune cells comprising a nucleic acid molecule encoding a chimeric NKG2D receptor and a) the cells further contain
   One or more endogenous genes encoding a NKG2D ligand that have been engineered to be inactivated;
   One or more shRNAs directed against the chimeric NKG2D receptor and/or one or more NKG2D ligands;
   And/or
b) the composition further contains
   One or more antibodies directed against the chimeric NKG2D receptor and/or one or more NKG2D ligands;
   An inhibitor of downstream signaling of the chimeric NKG2D receptor, particularly a PI3K inhibitor.

The methods for treatment can be autologous methods (the subject receives cells that originated from his or her body) or can be allogeneic methods (the immune cells are derived from a donor that is not the subject).

DETAILED DESCRIPTION

Definitions

Figure 1:
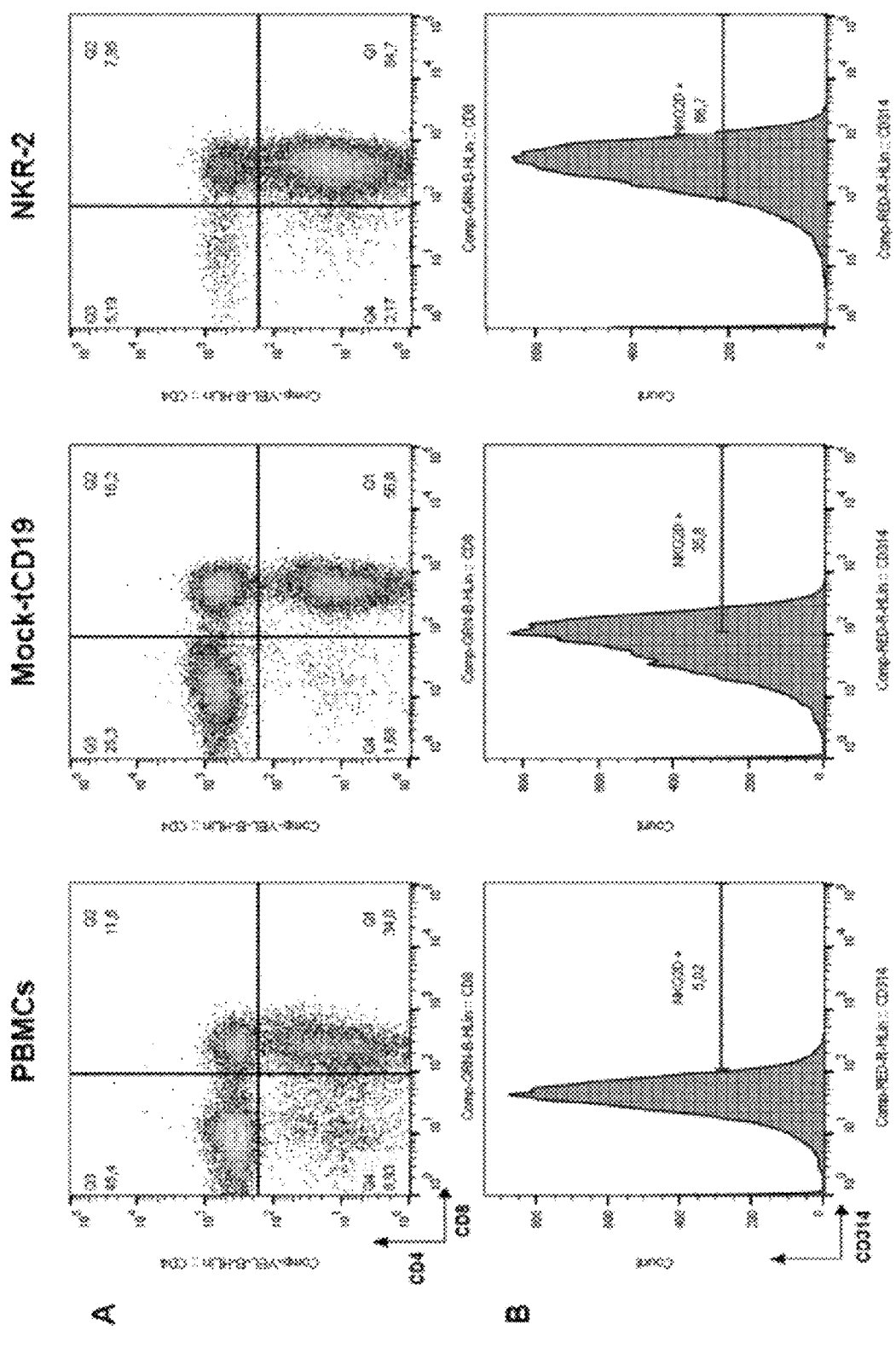
FIG. 1: Flow cytometric characterization of PBMCs, tCD19 and NKG2D-CAR T cells in a representative NKR-2 T cells process. Mononuclear cells purified from blood using density gradient method were analyzed before (PBMCs) and after (tCD19 and NKR-2 T cells) the NKR-2 T cells process. After acquisition, cells were gated on SSC/FSC for Lymphocytes. Lymphocytes were then gated on CD3. All CD3 positive cells were then displayed as followed: (A) CD4/CD8 distribution. (B) Surface expression of NKG2D (CD314).(C) Memory phenotype. CD62L and CD45RA for the distinction of Naïve (CD62L+CD45RA+), central memory (CD62L+CD45RA−), effector memory (CD62L−CD45RA−), and terminal differentiated T cells expressing CD45RA (CD62L− CD45RA+) and (D) Exhaustion phenotype as stained for CD223 (Lag-3) and CD279 (PD-1). One representative donor out of 3 is shown.
Figure 1:
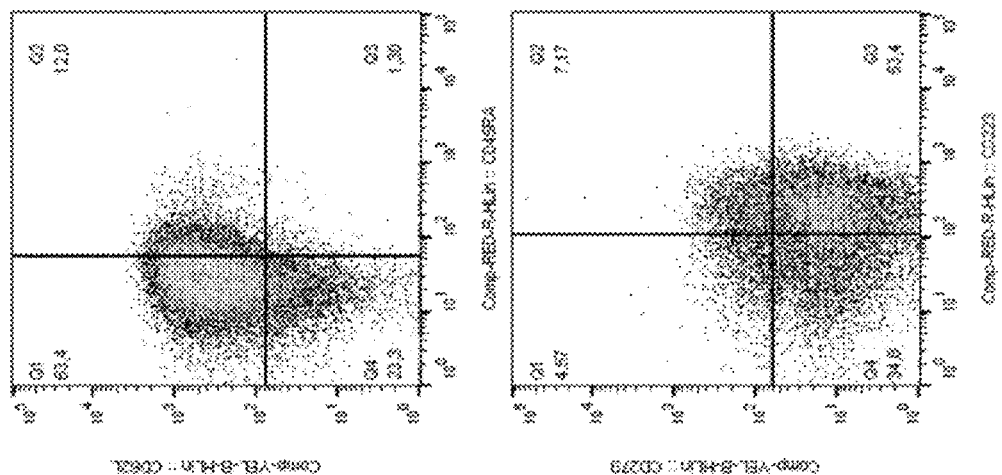
Figure 1:
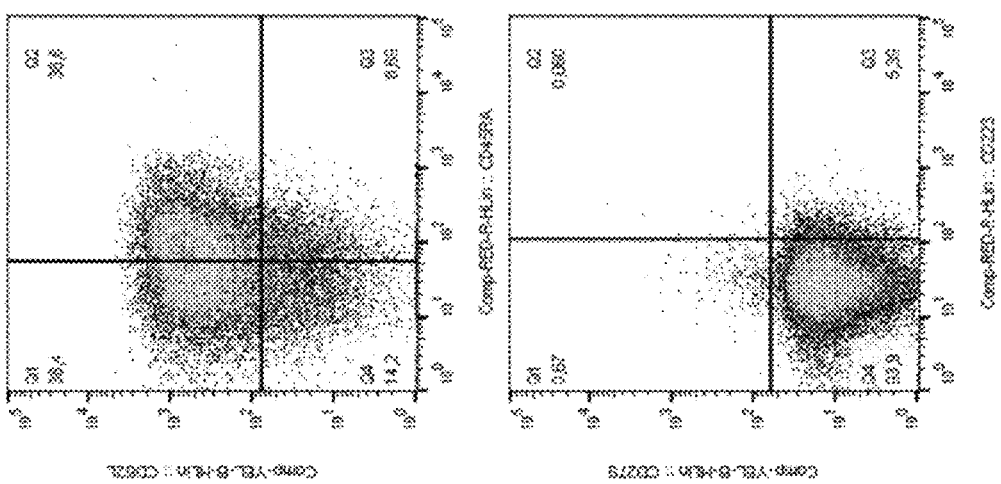
Figure 1:
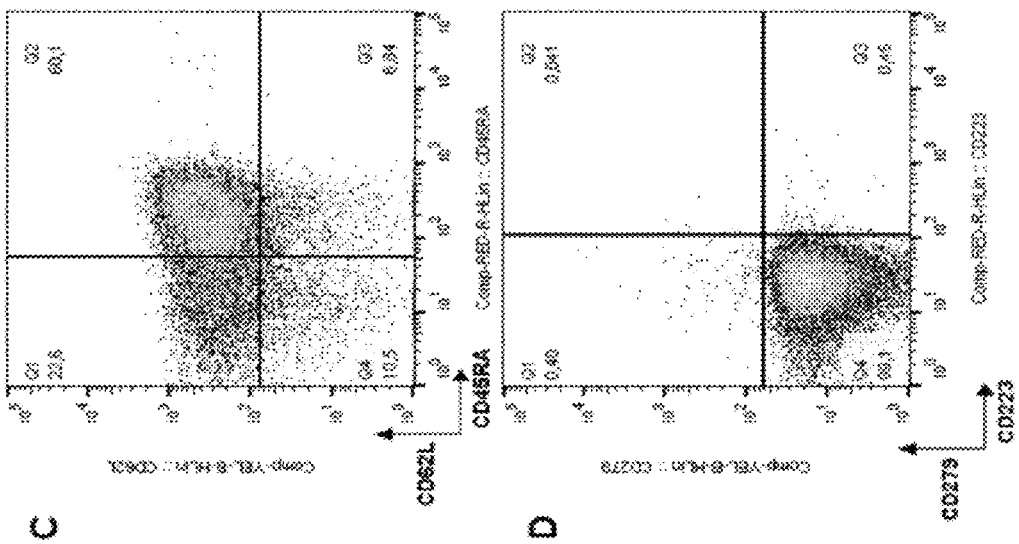

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention.

Unless specifically defined herein, all terms used herein have the same meaning as they would to one skilled in the art of the present invention. Practitioners are particularly directed to Green and Sambrook, Molecular Cloning: A Laboratory Manual, 4th ed., Cold Spring Harbor Laboratory Press. New York (2012); and Ausubel et al., Current Protocols in Molecular Biology (up to Supplement 114), John Wiley & Sons, New York (2016), for definitions and terms of the art. The definitions provided herein should not be construed to have a scope less than understood by a person of ordinary skill in the art.

The term "fratricide" as used herein refers to the killing of cells by genetically identical cells, most particularly immune cells.

The term "reducing and/or preventing fratricide" as used herein relates to the decrease in the occurrence of fratricide in a population of cells as compared to a suitable control population of cells (typically, but not necessarily, a population of identical cells in which no inhibition of NKG2D ligands takes place). Reduction can be expressed as a percentage reduction compared to control, e.g. there is 10%, 20%, 25%, 30%, 40%, 50%, 60%, 70%, 75%, 80%, 90% or even 100% less fratricide. Reduction of fratricide can also be evaluated by increase in final cell yield or number (since, when less cells are killed, more cells survive and can multiply). Thus, it can be evaluated e.g. by an increase in cell yield of 10%, 20%, 25%, 30%, 40%, 50%, 60%, 70%, 75%, 80%, 90%, 100% or even more than 100%. Importantly, reduction of fratricide as defined herein can also be evaluated by increase in antigen-specific cytokine production (e.g. interferon gamma secretion) and/or, in case of T cells, an increased frequency in memory phenotype of T cells (CD62L$^+$/CD45RA$^-$). While these measures may not directly correlate to absolute cell yield, if there is an increase in antigen-specific cytokine production, this means there are more therapeutically active cells at the end of the manufacturing process, which is equivalent to less fratricide in therapeutic cells. The same goes for increased frequency of T memory cells. Thus, reduction of fratricide can be evaluated by e.g. by an increase in antigen-specific cytokine production of 10%, 20%, 25%, 30%, 40%, 50%, 60%, 70%, 75%, 80%, 90%, 100% or even more than 100%. Or by an increased frequency of memory T cells of 10%, 20%, 25%, 30%, 40%, 50%, 60%, 70%, 75%, 80%, 90%, 100% or even more than 100%.

Measures to reduce fratricide can be taken prior to the fratricide process starts (which is generally preferred, as it is more effective) or during the fratricide killing. Preventing fratricide refers to measures taken before the fratricide process starts. According to particular embodiments, absolute prevention of fratricide means that no NKG2D-induced fratricide takes place (and ideally no fratricide takes place at all), equivalent to a 100% reduction in fratricide.

The term "immune cells" as used herein refers to cells that are part of the immune system (which can be either the adaptive or the innate immune system). Particularly envisaged immune cells include white blood cells (leukocytes), including lymphocytes, monocytes, macrophages and dendritic cells. Particularly envisaged lymphocytes include T cells, NK cells and B cells, most particularly envisaged are T cells. Immune cells as used herein are typically immune cells that are manufactured for adoptive cell transfer (either autologous transfer or allogeneic transfer). In the context of adoptive transfer, note that immune cells will typically be primary cells (i.e. cells isolated directly from human or animal tissue, and not or only briefly cultured), and not cell lines (i.e. cells that have been continually passaged over a long period of time and have acquired homogenous genotypic and phenotypic characteristics). According to specific embodiments, the immune cell is a primary cell. According to alternative specific embodiments, the immune cell is not a cell from a cell line.

The phrase "chimeric NKG2D receptor" as used herein refers to a non-naturally occurring receptor that has a specificity for NKG2D ligands. It is chimeric as the binding moiety is fused to one or more distinct moieties (including at least a signaling moiety) of which at least one moiety is from a different origin (e.g. a different protein) than the binding moiety. Particularly envisaged examples of chimeric NKG2D receptors include NKG2D CARs, i.e. chimeric antigen receptors with a binding moiety derived from the NKG2D receptor. Such NKG2D CARs have e.g. been described in WO2006/036445 and WO2014/117121. Also included in the definition of chimeric NKG2D receptor herein are CARs that have a binding moiety recognizing one or more NKG2D ligands that is not derived from the NKG2D receptor, e.g. an antibody against one or more NKG2D ligands, or an antibody-like moiety (e.g. an scFv, a VHH, a sdAb or the like). This is then typically fused to a signaling moiety that transduces a signal in an immune cell, particularly a T cell (such as a CD3 zeta chain or a Fc epsilon receptor gamma chain).

The term "functional inhibition of NKG2D signaling" as used in the application refers to interference with the function of the NKG2D gene product (i.e. the product of the chimeric NKG2D receptor gene), either at the DNA level (by inhibiting the formation of NKG2D gene product or of one or more of its ligands, i.e. by preventing or interfering with transcription), at the RNA level (by neutralizing or destabilizing mRNA to prevent or interfere with translation—the mRNA can also be of the chimeric NKG2D receptor and/or of one or more of the NKG2D ligands) or at the protein level (by neutralizing or inhibiting the chimeric NKG2D protein and/or one or more of its ligands). Neutralizing at the protein level can be achieved at the cellular surface (e.g. by inhibiting receptor-ligand interaction) or before the protein is expressed at the surface (e.g. by retaining the protein in an intracellular organelle). Typically, the ultimate functional effect of inhibition of NKG2D-induced signalling will be inhibition of immune cell activation through signals generated by the chimeric NKG2D receptor, although this can be achieved indirectly (e.g. at the DNA level, or by inhibition of one or more ligands).

Functional inhibition of NKG2D signaling does not necessarily mean complete ablation of the NKG2D-induced signal, although this is envisaged as well. Particularly with antisense RNA and siRNA, but with antibodies as well, it is known that inhibition is often partial inhibition rather than complete inhibition. However, lowering functional NKG2D gene product or NKG2D ligand levels may have a beneficial effect even when complete inhibition is not achieved— particularly as fratricide is typically cell density-dependent, and thus reduced functional ligand or receptor availability may lead to perceived lower cell density. (Note that lowering the actual cell density by using culture dilution is not feasible to generate a suitable product in view of the large numbers of cells needed for future clinical trials).

Thus, according to particular embodiments, the inhibition will result in a decrease of 10%, 20%, 25%, 30%, 40%, 50%, 60%, 70%, 75%, 80%, 90% or up to 100% of functional chimeric NKG2D receptor gene product, or of one or more of NKG2D ligands. Methods of measuring the levels of functional NKG2D receptor gene product or ligands are known to the skilled person, and these can be measured before and after the addition of the inhibitor to assess the decrease in levels of functional gene product.

The term "transient inhibition" as used herein means that the inhibition is temporary (or temporally regulated), and function of the chimeric NKG2D receptor is restored at a later time point. Typically, NKG2D-induced signaling will be inhibited during manufacture of immune cells (i.e. prior to them being used as a medicament), while signaling capacity will be restored once the cells will be administered to the patient. This because the NKG2D-mediated signaling is important for therapeutic efficacy.

The term "NKG2D ligands" as used in the application refers to the human genes MICA (Gene ID: 100507436), MICB (Gene ID: 4277), ULBP1 (Gene ID: 80329), ULBP2 (Gene ID: 80328), ULBP3 (Gene ID: 79465), ULBP4 or RAET1E (Gene ID: 135250), ULBP5 or RAET1G (Gene ID: 353091), ULBP6 or RAET1L (Gene ID: 154064) and their gene products (or the relevant homolog when cells of other species are used).

The present application is the first to show that fratricide of immune cells expressing a chimeric NKG2D receptor can be prevented or reduced by inhibiting the function of this receptor (by inhibiting either the receptor, or one or more of its ligands, or both). Such reduction in fratricide enhances yield of the cells and reduces cost of the therapy, thus facilitating the availability of the therapy in a clinical setting.

Said inhibition can be transient (during the in vitro manufacturing process of the immune cells, but not when administered to a patient—as the chimeric NKG2D receptor is needed for therapeutic immune cell function of said cells) or can be permanent (when only the ligands in the immune cells are inhibited, as this does not interfere with therapeutic efficacy).

Accordingly, it is an object of the invention to provide methods of reducing and/or preventing fratricide during manufacturing of immune cells expressing a chimeric NKG2D receptor, comprising functional inhibition of NKG2D signaling during the manufacturing process of the cells. These manufacturing methods are performed in vitro or ex vivo. Likewise, methods of reducing and/or preventing fratricide during freeze/thaw cycles of immune cells expressing a chimeric NKG2D receptor, comprising functional inhibition of NKG2D signaling during the freeze/thaw cycles are provided. These freeze/thaw methods also are performed in vitro or ex vivo.

Of note, although NKG2D is the best studied receptor involved in recognition of induced-self antigens, it is not the only receptor in this family that recognizes stress-induced ligands (or induced self antigens, or markers of the abnormal self, all used as equivalents herein). Other receptors that are able to bind induced-self antigens are NKG2C, NKG2E, NKG2F, NKG2H (like NKG2D, all CD94 molecules) or Natural Cytotoxicity Receptors (NCR) such as NKp 46, NKp30 and NKp44, and it is envisaged that the methods and compositions can be used for such chimeric receptors as well, mutatis mutandis. Thus, wherever NKG2D is used in the application, this also applies to NKG2C, NKG2E, NKG2F, NKG2H, NKp46, NKp30 and NKp44. Note that the ligands for NKG2C, E, F and H are nonclassical MHC glycoproteins class I (HLA-E in human).

These methods are in vitro methods (since they coincide with the manufacturing of the cells).

Functional inhibition of NKG2D signaling is achieved by one or more of:
  Permanent or transient inhibition of one or more of the NKG2D ligands of the immune cells;
  Transient inhibition of the chimeric NKG2D receptor;
  Transient inhibition of downstream signaling of the chimeric NKG2D receptor.

Inhibition can occur in multiple ways: contact inhibition (competitive inhibition or non-competitive inhibition), inhibition by interfering with ligand or receptor expression, interfering with ligand or receptor localization (e.g. preventing migration to cell surface), inhibition by binding to ligand or receptor or preventing interaction of both, and inhibition of downstream signaling, to name a few.

Permanent inhibition of the one or more of the NKG2D ligands is typically achieved by genetic knockdown. It has indeed been shown that gene editing is one potential method to specifically eliminate target antigen expression in the engineered T cell(14). However, given the potential expression of eight different ligands, gene editing technology to eliminate all these polymorphic targets presents a challenge, so it is particularly envisaged when only one or a few ligands need to be permanently inactivated. If more ligands are expressed, one of the alternative strategies may be better suited to control fratricide. The instant inventors have identified that, of the eight NKG2D ligands, MICA and MICB are the ones predominantly expressed on the cell surface of CD4+ and CD8+ human T cells. Thus, according to particular embodiments, particularly inhibition of MICA and MICB is envisaged.

In general, functional inhibition can be achieved at three levels. First, at the DNA level, e.g. by removing or disrupting a gene (typically a NKG2D ligand gene) in said immune cells, or preventing transcription to take place (in both instances preventing synthesis of the gene product). Second, at the RNA level, e.g. by preventing efficient translation to take place—this can be through destabilization of the mRNA so that it is degraded before translation occurs from the transcript, or by hybridizing to the mRNA. Third, at the protein level, e.g. by binding to the protein, inhibiting its function, retaining the protein at a different cellular location and/or marking the protein for degradation.

If inhibition is to be achieved at the DNA level, this may be done using gene therapy to knock-out or disrupt the gene. As this typically results in permanent inhibition, this is particularly envisaged for inhibition of NKG2D ligands in the immune cells. As used herein, a "knock-out" can be a gene knockdown or the gene can be knocked out by a mutation such as, a point mutation, an insertion, a deletion, a frameshift, or a missense mutation by techniques known in the art, including, but not limited to, retroviral gene transfer. Another way in which genes can be knocked out is by the use of engineered nucleases. Examples of such engineered nucleases include, but are not limited to, meganucleases, zinc finger nucleases, TALENs, megaTALs and CRISPR nucleases.

Meganucleases, found commonly in microbial species, have the unique property of having very long recognition sequences (>14 bp) for making site-specific double strand breaks in nucleic acids. This makes them naturally very specific for a target sequence, and through mutagenesis and high throughput screening, hybrid meganuclease variants can be made that recognize unique sequences. As opposed to meganucleases, the concept behind ZFNs and TALEN technology is based on a non-specific DNA cutting enzyme, which can then be linked to specific DNA sequence recognizing peptides such as zinc fingers and transcription activator-like effectors (TALEs). Zinc-finger nucleases (ZFNs) are artificial restriction enzymes generated by fusing a zinc finger DNA-binding domain to a DNA-cleavage domain. Zinc finger domains can be engineered to target desired DNA sequences, which enable zinc-finger nucleases to target unique sequence within a complex genome. By taking advantage of endogenous DNA repair machinery, these reagents can be used to precisely alter the genomes of higher organisms. TALENs work similar to zinc fingers, but rely on transcription activator-like effectors (TALEs) for DNA recognition. TALEs are found in repeats with a one-to-one recognition ratio between the amino acids and the recognized nucleotide pairs. Because TALEs happen in repeated patterns, different combinations can be tried to create a wide variety of sequence specificities.

MegaTALs are derived from the combination of two distinct classes of DNA targeting enzymes. Meganucleases (also referred to as homing endonucleases) are single peptide chains that have the advantage of both DNA recognition and nuclease functions in the same domain. However, meganuclease target recognition is difficult to modify, and they often have reduced specificity and lower on-target cleavage efficiency than other genome targeting endonucleases. Transcription activator-like (TAL) effectors are DNA recognizing proteins that have been linked to separate DNA endonuclease domains in order to achieve a targeted DNA double strand break. In contrast to meganucleases, TALs are easily engineered to target specific DNA sequences. Current platforms rely on a pair of TAL effectors, each coupled to a non-specific DNA cleavage domain, in which DNA cleavage only occurs when both TAL effectors bind their respective sequences and the two endonuclease domains dimerize in order to cleave the DNA. However, TAL effector nucleases can cause off-target activity, are much larger than meganucleases, and require the delivery of two separate proteins. A megaTAL is the unification of a TAL effector with a meganuclease.

CRISPR/Cas (Clustered Regularly Interspaced Short Palindromic Repeats/Crispr associated protein) is a genome editing technology using a modified version of a prokaryotic defence mechanism, and allows permanent modification of genes within organisms. By delivering the Cas (typically Cas9) nuclease complexed with a synthetic guide RNA (gRNA) into a cell, the cell's genome can be cut at a desired location, allowing existing genes to be removed and/or new ones added.

Permanent inhibition by genetic knockdown of one or more NKG2D ligand genes is typically done in the immune cells where the chimeric NKG2D receptor is also present. One or more NKG2D ligand genes may mean inhibition of any combination of MICA, MICB, ULBP1, ULBP2, ULBP3, ULBP4, ULBP5 and ULBP6; and thus may mean knockout of one, two, three, four, five, six, seven or eight genes.

Apart from permanent inhibition of NKG2D ligands, functional inhibition of NKG2D signaling can also be achieved by transient inhibition. Transient inhibition may be inhibition of one or more NKG2D ligands on the immune cells, but also inhibition of the chimeric NKG2D receptor or inhibition of downstream signaling.

The timeframe of the transient inhibition will typically coincide with the timeframe of manufacturing. Manufacturing of immune cells that express a chimeric NKG2D receptor involves several steps, and protocols may vary, but in essence they will always contain a transduction step (in which the chimeric NKG2D receptor is introduced in the isolated immune cells), an expansion step (in which the cells are cultured and increase in number) and a harvesting step (in which the cells are isolated and reformulated or concentrated, prior to administration to a patient or for (cryo) preservation). Transient inhibition will particularly mean inhibition during the expansion step, as this is the time when fratricide is most likely to occur, but transient can be during the entire manufacturing process (from or even before the transduction step up to the harvesting step or beyond). Typically, when external inhibitors are used (e.g. antibodies), these will be removed during the harvesting/reformulation process. Thus, the methods may involve an active step of removal of the inhibitors used. In other instances however, inhibitors may be transient by nature (e.g. because of a short half-life) or are under control of an inducible promoter that is no longer active after the manufacturing process, so no active step may be needed to end the inhibition of functional NKG2D signaling. In a typical set-up, transient inhibition will entail inhibition from about the transduction step up to the administration/infusion step, but shorter or longer timeframes can be envisaged as well.

One form of transient inhibition is by transient gene inactivation. Transient gene inactivation may for instance be achieved through expression of antisense RNA in the immune cells, or by administering antisense RNA to said cells. An antisense construct can be delivered, for example, as an expression plasmid, which, when transcribed in the cell, produces RNA that is complementary to at least a unique portion of the target mRNA (here mRNA of a NKG2D ligand or of the chimeric NKG2D receptor).

A more rapid method for the inhibition of gene expression is based on the use of shorter antisense oligomers consisting of DNA, or other synthetic structural types such as phosphorothiates, 2'-O-alkylribonucleotide chimeras, locked nucleic acid (LNA), peptide nucleic acid (PNA), or morpholinos. With the exception of RNA oligomers, PNAs and morpholinos, all other antisense oligomers act in eukaryotic cells through the mechanism of RNase H-mediated target cleavage. PNAs and morpholinos bind complementary DNA and RNA targets with high affinity and specificity, and thus act through a simple steric blockade of the RNA translational machinery, and appear to be completely resistant to nuclease attack. An "antisense oligomer" refers to an antisense molecule or anti-gene agent that comprises an oligomer of at least about 10 nucleotides in length. In embodiments an antisense oligomer comprises at least 15, 18 20, 25, 30, 35, 40, or 50 nucleotides. Antisense approaches involve the design of oligonucleotides (either DNA or RNA, or derivatives thereof) that are complementary to an mRNA encoded by polynucleotide sequences of FMR1. Antisense RNA may be introduced into a cell to inhibit translation of a complementary mRNA by base pairing to it and physically obstructing the translation machinery. This effect is therefore stoichiometric. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense polynucleotide sequences, a single strand of the duplex DNA may thus be tested, or triplex formation may be assayed. The ability to hybridize will depend on both the degree of complementarity and the length of the antisense polynucleotide sequence. Generally, the longer the hybridizing polynucleotide sequence, the more base mismatches with an RNA it may contain and still form a stable duplex (or triplex, as the case may be). One skilled in the art can ascertain a tolerable degree of mismatch by use of standard procedures to determine the melting point of the hybridized complex. Oligomers that are complementary to the 5' end of the message, e.g., the 5' untranslated region (UTR) up to and including the AUG translation initiation codon, should work most efficiently at inhibiting translation. However, sequences complementary to the 3' UTR of mRNAs have recently been shown to be effective at inhibiting translation of mRNAs as well (Wagner, R. (1994) Nature 372, 333-335). Therefore, oligomers complementary to either the 5', 3' UTRs, or non-coding regions of the target gene could be used in an antisense approach to inhibit translation of said endogenous mRNA encoded by the target gene. Oligomers complementary to the 5' UTR of said mRNA should include the complement of the AUG start codon. Antisense oligomers complementary to mRNA coding regions are less efficient inhibitors of translation but could be used in accordance with the invention. Whether designed to hybridize to the 5', 3' or non-coding region of a said mRNA, antisense oligomers should be at least 10 nucleotides in length, and are preferably oligomers ranging from 15 to about 50 nucleotides in length. In certain embodiments, the oligomer is at least 15 nucleotides, at least 18 nucleotides, at least 20 nucleotides, at least 25 nucleotides, at least 30 nucleotides, at least 35 nucleotides, at least 40 nucleotides, or at least 50 nucleotides in length. A related method uses ribozymes instead of antisense RNA. Ribozymes are catalytic RNA molecules with enzyme-like cleavage properties that can be designed to target specific RNA sequences. Successful target gene inactivation, including temporally and tissue-specific gene inactivation, using ribozymes has been reported in mouse, zebrafish and fruit-flies. RNA interference (RNAi) is a form of post-transcriptional gene silencing. The phenomenon of RNA interference was first observed and described in *Caenorhabditis elegans* where exogenous double-stranded RNA (dsRNA) was shown to specifically and potently disrupt the activity of genes containing homologous sequences through a mechanism that induces rapid degradation of the target RNA. Several reports describe the same catalytic phenomenon in other organisms, including experiments demonstrating spatial and/or temporal control of gene inactivation, including plant (*Arabidopsis thaliana*), protozoan (*Trypanosoma bruceii*), invertebrate (*Drosophila melanogaster*), and vertebrate species (*Danio rerio* and *Xenopus laevis*). The mediators of sequence-specific messenger RNA degradation are small interfering RNAs (siRNAs) generated by ribonuclease Ill cleavage from longer dsRNAs. Generally, the length of siRNAs is between 20-25 nucleotides (Elbashir et al. (2001) Nature 411, 494-498). The siRNA typically comprise a sense RNA strand and a complementary antisense RNA strand annealed together by standard Watson Crick base pairing interactions (hereinafter "base paired"). The sense strand comprises a nucleic acid sequence that is identical to a target sequence contained within the target mRNA. The sense and antisense strands of the present siRNA can comprise two complementary, single stranded RNA molecules or can comprise a single molecule in which two complementary portions are base paired and are covalently linked by a single stranded "hairpin" area (often referred to as shRNA). The term "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

The siRNAs of the invention can comprise partially purified RNA, substantially pure RNA, synthetic RNA, or recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA of the invention can also comprise a 3' overhang. A "3' overhang" refers to at least one unpaired nucleotide extending from the 3' end of an RNA strand. Thus, in one embodiment, the siRNA of the invention comprises at least one 3' overhang of from one to about six nucleotides (which includes ribonucleotides or deoxynucleotides) in length, preferably from one to about five nucleotides in length, more preferably from one to about four nucleotides in length, and particularly preferably from about one to about four nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is two nucleotides in length. In order to enhance the stability of the present siRNAs, the 3' overhangs can also be stabilized against degradation. In one embodiment, the overhangs are stabilized by including purine nucleotides, such as adenosine or guanosine nucleotides.

Alternatively, substitution of pyrimidine nucleotides by modified analogues, e.g., substitution of uridine nucleotides in the 3' overhangs with 2' deoxythymidine, is tolerated and does not affect the efficiency of RNAi degradation. In particular, the absence of a 2' hydroxyl in the 2' deoxythymidine significantly enhances the nuclease resistance of the 3' overhang in tissue culture medium.

siRNAs can be obtained using a number of techniques known to those of skill in the art. For example, the siRNAs can be chemically synthesized or recombinantly produced using methods known in the art. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, siRNA can also be expressed from recombinant circular or linear DNA plasmids using any suitable promoter. Suitable promoters for expressing siRNA of the invention from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment. The siRNA expressed from recombinant plasmids can either be isolated from cultured cell expression systems by standard techniques, or can be expressed intracellularly, e.g. in breast tissue or in neurons.

The siRNAs of the invention can also be expressed intracellularly from recombinant viral vectors. The recombinant viral vectors comprise sequences encoding the siRNAs of the invention and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in the tissue where the tumour is localized.

As used herein, an "effective amount" of the siRNA is an amount sufficient to cause RNAi mediated degradation of the target mRNA, or an amount sufficient to reduce NKG2D signaling. RNAi mediated degradation of the target mRNA can be detected by measuring levels of the target mRNA or protein in the cells of a subject, using standard techniques for isolating and quantifying mRNA or protein as described above.

It has been shown that morpholino antisense oligonucleotides in zebrafish and frogs overcome the limitations of RNase H-competent antisense oligonucleotides, which include numerous non-specific effects due to the non target-specific cleavage of other mRNA molecules caused by the low stringency requirements of RNase H. Morpholino oligomers therefore represent an important new class of antisense molecule. Oligomers of the invention may be synthesized by standard methods known in the art. As examples, phosphorothioate oligomers may be synthesized by the method of Stein et al. (1988) Nucleic Acids Res. 16, 3209-3021), methylphosphonate oligomers can be prepared by use of controlled pore glass polymer supports (Sarin et al. (1988) Proc. Natl. Acad. Sci. USA. 85, 7448-7451). Morpholino oligomers may be synthesized by the method of Summerton and Weller U.S. Pat. Nos. 5,217,866 and 5,185,444.

Inhibition, particularly transient inhibition, can also be achieved by inhibitors at the protein level. A typical example thereof are antibodies against the chimeric NKG2D receptor, or antibodies against one or more of the NKG2D ligands.

The term 'antibody' or 'antibodies' relates to an antibody characterized as being specifically directed against the NKG2D receptor, NKG2D ligand or any functional derivative thereof, with said antibodies being preferably monoclonal antibodies; or an antigen-binding fragment thereof, of the F(ab')2, F(ab) or single chain Fv type, or any type of recombinant antibody derived thereof. These antibodies of the invention, including specific polyclonal antisera prepared against the target protein or any functional derivative thereof, have no cross-reactivity to other proteins. The monoclonal antibodies of the invention can for instance be produced by any hybridoma liable to be formed according to classical methods from splenic cells of an animal, particularly of a mouse or rat immunized against the target protein or any functional derivative thereof, and of cells of a myeloma cell line, and to be selected by the ability of the hybridoma to produce the monoclonal antibodies recognizing the target protein or any functional derivative thereof which have been initially used for the immunization of the animals. The monoclonal antibodies according to this embodiment of the invention may be humanized versions of the mouse monoclonal antibodies made by means of recombinant DNA technology, departing from the mouse and/or human genomic DNA sequences coding for H and L chains or from cDNA clones coding for H and L chains. Alternatively the monoclonal antibodies according to this embodiment of the invention may be human monoclonal antibodies. Such human monoclonal antibodies are prepared, for instance, by means of human peripheral blood lymphocytes (PBL) repopulation of severe combined immune deficiency (SCID) mice as described in PCT/EP 99/03605 or by using transgenic non-human animals capable of producing human antibodies as described in U.S. Pat. No. 5,545,806. Also fragments derived from these monoclonal antibodies such as Fab, F(ab)'2 and scFv ("single chain variable fragment"), providing they have retained the original binding properties, form part of the present invention. Such fragments are commonly generated by, for instance, enzymatic digestion of the antibodies with papain, pepsin, or other proteases. It is well known to the person skilled in the art that monoclonal antibodies, or fragments thereof, can be modified for various uses. The antibodies involved in the invention can be labeled by an appropriate label of the enzymatic, fluorescent, or radioactive type. In a particular embodiment said antibodies against a target protein or a functional fragment thereof are derived from camels. Camel antibodies are fully described in WO94/25591, WO94/04678 and in WO97/49805.

Other inhibitors of NKG2D signaling at the protein level include, but are not limited to, peptide inhibitors of NKG2D ligands or of the chimeric receptor, peptide-aptamer (Tomai et al., J Biol Chem. 2006) inhibitors of NKG2D ligands or of the chimeric NKG2D receptor, and protein interferors or Pept-Ins™ as described in WO2007/071789 or WO2012/123419, incorporated herein by reference.

Another way of inhibition at the protein level is by interfering with the secretory transport, so that the receptor and/or ligands are not transported to the cell membrane. Typically, this is a temporary form of inhibition and normal cellular location can be restored when the appropriate signal is given to the cells. An exemplary method according to this principle is the RUSH (retention using selective hooks) system (Boncompain et al., Nature Methods 2012 and WO2010142785). This is particularly envisaged for transient inhibition of the chimeric NKG2D receptor.

Small molecule inhibitors, e.g. small organic molecules, and other drug candidates can be obtained, for example, from combinatorial and natural product libraries.

Particularly envisaged for transient inhibition of functional NKG2D signaling is the inhibition of the downstream signal through the chimeric NKG2D receptor. It is demonstrated herein that an important part of the observed fratricide is mediated through the NKG2D-induced PI3K signaling pathway, which is the main signaling pathway of the NKG2D/DAP10 complex. Thus, inhibition of PI3K signaling effectively is functional inhibition of NKG2D signaling, as it reduces the functional effect of ligand-receptor binding. Transient inhibition of downstream signaling can thus be achieved by transient inhibition of PI3K signaling. Exemplary inhibitors include commercially available PI3K inhibitors. One particularly envisaged inhibitor is the broad range PI3K inhibitor LY294002. Another particularly envisaged inhibitor is Cal101 (idelalisib). Other examples include e.g. Copanlisib, Taselisib, Buparlisib, Duvelisib, Alpelisib, and Umbralisib.

The methods described herein are applicable during manufacturing of NKG2D-expressing immune cells. Typically, manufacturing of immune cells occurs when cells are being prepared or cultured for adoptive transfer. This can be autologous adoptive transfer (a subject receives his own cells that have been modified and/or expanded), or allogeneic adoptive transfer (a subject receives cells from a different individual).

Many different types of immune cells are used for adoptive therapy and thus are envisaged for use in the methods described herein. Examples of immune cells include, but are not limited to, T cells, NK cells, NKT cells, lymphocytes, stem cells or iPSCs. The latter two are not immune cells as such, but can be used in adoptive cell transfer for immunotherapy (see e.g. Jiang et al., Cell Mol Immunol 2014; Themeli et al., Cell Stem Cell 2015). Typically, while the manufacturing starts with stem cells or iPSCs (or may even start with a dedifferentiation step from immune cells towards iPSCs), manufacturing will entail a step of differentiation to immune cells prior to administration. As the instant methods relate to the manufacturing process (i.e., the steps prior to administration), stem cells and iPSCs used in manufacturing of immune cells for adoptive transfer are considered as immune cells herein. According to particular embodiments, the stem cells envisaged in the methods do not involve a step of destruction of a human embryo.

Particularly envisaged cells for use in the instant methods are T cells and NK cells.

According to a further aspect, engineered immune cells are provided wherein fratricide is reduced and/or prevented. These cells are characterized by functional inhibition of NKG2D signalling within the cells, e.g. through knockout of NKG2D ligands, permanent or transient inhibition of NKG2D ligands, or transient inhibition of a chimeric receptor (e.g. by expression of transient inhibitors, transient expression of inhibitors, or temporary retention of receptor or ligands).

Accordingly, these cells comprise a nucleic acid molecule encoding a chimeric NKG2D receptor and at least one of:
One or more endogenous genes encoding a NKG2D ligand that have been engineered to be inactivated;
One or more inhibitors directed against the chimeric NKG2D receptor and/or one or more NKG2D ligands;
a binding tag fused to the chimeric NKG2D receptor and/or to one or more NKG2D ligands.

The binding tag (e.g. streptavidin) can be used in methods like RUSH (retention using selective hooks) system (Boncompain et al., Nature Methods 2012 and WO2010142785) and is particularly envisaged for transient inhibition of the chimeric NKG2D receptor.

Particularly envisaged are cells that comprise a nucleic acid molecule encoding a chimeric NKG2D receptor and at least one of:
One or more endogenous genes encoding a NKG2D ligand that have been engineered to be inactivated;
One or more inhibitors directed against the chimeric NKG2D receptor and/or one or more NKG2D ligands.

The inactivation of endogenous genes can be done as described above, e.g. using genome editing, engineered nucleases such as CRISPR/Cas, TALEN, Zinc finger nucleases, meganucleases, MegaTAL nucleases or other suitable methods (including, but not limited to Cre/Lox or Flp/FRT based systems). Although not a prerequisite, in most cases the inactivated endogenous genes will be inactivated permanently (i.e. with no obvious reversal of the inactivation). This is why this method is particularly suited for inactivation of ligands (that are not needed for the immune cells to exert their immunotherapeutic effect), but less for the inactivation of NKG2D receptor—as the receptor is needed for its role in immunotherapy.

Cells that comprise an inhibitor will typically comprise a plasmid encoding the inhibitor, as this is the most convenient way to ensure the inhibitor is comprised in the cells. Thus, it is particularly envisaged that the inhibitor can be expressed from a plasmid. While this can be done with antibodies or peptides, most particularly envisaged are nucleic acid inhibitors, for instance RNA interference technologies such as siRNA or shRNA. The inhibitor (such as the RNA inhibitor) can be directed against the chimeric NKG2D receptor and/or against one or more NKG2D ligands. These NKG2D ligands are selected from the group consisting of MICA, MICB, ULBP1, ULBP2, ULBP3, ULBP4, ULBP5 and ULBP6.

The cells may be provided as such, or as a composition. Compositions may also be provided wherein NKG2D signaling is functionally inhibited by adding an (external) inhibitor to the cells—one that is taken up by the cells, or that performs its inhibitory role extracellularly. Thus, according to a further aspect, compositions are provided of immune cells expressing a chimeric NKG2D receptor and further comprising an inhibitor. These cells may comprise one or more endogenous genes encoding a NKG2D ligand that have been engineered to be inactivated; and/or one or more inhibitors directed against the chimeric NKG2D receptor and/or one or more NKG2D ligands that are encoded as nucleic acids in the cells, and/or a binding tag fused to the chimeric NKG2D receptor and/or to one or more NKG2D ligands ('internal inhibitors', as detailed above).

Additionally or alternatively, the compositions may contain one or more inhibitors directed against the chimeric NKG2D receptor and/or one or more NKG2D ligands (that are not encoded as nucleic acids in the cells); and/or an inhibitor of downstream signaling of the chimeric NKG2D receptor ('external inhibitors').

Particularly envisaged inhibitors directed against the chimeric NKG2D receptor and/or one or more NKG2D ligands include antibodies directed against these proteins. Particularly envisaged inhibitors of downstream signaling of the chimeric NKG2D receptor include PI3K inhibitors.

In both cases, the inhibitors may be contained within the cells, or the compositions contain the immune cells and inhibitors as separate ingredients, i.e. outside of the cells. Note that, even though the compositions can be provided as separate ingredients, inhibitors may be taken up by the immune cells. For instance, inhibitors of downstream signaling such as PI3K inhibitors are often small molecules that are easily taken up by cells. Antibodies may or may not be taken up by cells, but as the interaction between the NKG2D receptor and its ligands occurs outside the cell, cellular uptake is not a prerequisite for inhibition, as e.g. competitive inhibitors may function outside of the cells.

According to a further aspect, the engineered immune cells or compositions described herein are provided for use as a medicament. According to still a further aspect, the engineered immune cells or compositions described herein are provided for use in the treatment of diseases characterized by NKG2D ligand expression. It is well documented that NKG2D ligands such as MICA, MICB or those of the RAET1/ULBP family are induced self-antigens, i.e. they are cell ligands that are expressed in abnormal conditions or conditions of cellular stress, most particular in stressed (e.g. inflamed), transformed or infected cells. Accordingly, the cells or compositions are provided for use in the treatment of diseases selected from inflammatory disease, cancer, or infection (e.g. viral, bacterial, fungal infection). As cell therapy is quite expensive, it is particularly envisaged for life-threatening diseases. Accordingly, most particularly, the cells and compositions described herein are provided for use in the treatment of cancer. Whereas in principle all cancers can be treated, including, but not limited to, bladder cancer, brain cancer, breast cancer, cervical cancer, colorectal cancer, esophageal cancer, glioblastoma, head and neck cancer, kidney cancer, leukemia, liver cancer, lung cancer, lymphoma, melanoma, mesothelioma, multiple myeloma, ovarian cancer, pancreatic cancer, prostate cancer, sarcoma, stomach cancer and thyroid cancer; most particularly envisaged cancers include leukemia (including AML), multiple myeloma, bladder cancer, breast cancer, colorectal cancer, ovarian cancer, and pancreatic cancer. This because these 7 cancers typically have high NKG2D ligand expression.

That the cells and compositions are provided for use in treatment is equivalent as saying that methods of treating disease are provided, comprising a step of administering these cells or compositions to a subject in need thereof. Thus, methods of treating inflammatory disease, cancer, or infection are provided comprising administering the cells Particularly envisaged are methods of treating cancer in a subject in need thereof, comprising a step of administering an engineered immune cell to said subject, the immune cell containing a non-native nucleic acid molecule encoding a chimeric NKG2D receptor and at least one of:
  One or more endogenous genes encoding a NKG2D ligand that have been engineered to be inactivated;
  One or more inhibitors directed against the chimeric NKG2D receptor and/or one or more NKG2D ligands;
  a binding tag fused to the chimeric NKG2D receptor and/or to one or more NKG2D ligands.

Even more particularly envisaged are methods of treating cancer in a subject in need thereof, comprising a step of administering an engineered immune cell to said subject, the immune cell containing a non-native nucleic acid molecule encoding a chimeric NKG2D receptor and at least one of:
  One or more endogenous genes encoding a NKG2D ligand that have been engineered to be inactivated;
  One or more inhibitors directed against the chimeric NKG2D receptor and/or one or more NKG2D ligands.

Likewise, methods of treating cancer in a subject in need thereof are provided, comprising a step of administering a composition to said subject, wherein the composition comprises immune cells expressing a chimeric NKG2D receptor and one or more of:
  one or more endogenous genes encoding a NKG2D ligand that have been engineered to be inactivated; and/or
  one or more inhibitors directed against the chimeric NKG2D receptor and/or one or more NKG2D ligands that are encoded as nucleic acids in the cells, and/or
  a binding tag fused to the chimeric NKG2D receptor and/or to one or more NKG2D ligands; and/or
  one or more inhibitors directed against the chimeric NKG2D receptor and/or one or more NKG2D ligands (that are not encoded as nucleic acids in the cells); and/or
  an inhibitor of downstream signaling of the chimeric NKG2D receptor.

The immune cells may be autologous to the subject to which the cells are to be administered, or may be allogeneic, i.e. originating from a different subject.

It is to be understood that although particular embodiments, specific configurations as well as materials and/or molecules, have been discussed herein for cells and methods according to present invention, various changes or modifications in form and detail may be made without departing from the scope and spirit of this invention. The following examples are provided to better illustrate particular embodiments, and they should not be considered limiting the application. The application is limited only by the claims.

EXAMPLES

Introduction

Given the plethora of NKG2D ligands that could be expressed in T cells, genetic editing to eliminate all ligand expression was not deemed the most efficient option. Consequently, alternative strategies to control fratricide have been investigated to facilitate the delivery of NKG2D targeted CAR T cell therapy. Two differing approaches were explored, using a signaling inhibitor or an antibody-based approach. Both resulted in inhibition of fratricide, albeit to a different extent.

Inclusion of a Phosphoinositol-3-Kinase inhibitor (LY294002) blunted the fratricide effect and provided a generic means of generating NKR-2 CART cells. Use of the PI3K inhibitor further enhanced NKR-2 driven potency and shifted the cells to a memory phenotype. A target specific approach involving antibody blockade of the CAR itself elicited a further improvement in NKR-2 CAR T cell yield, with a reduction in potency and a change in CD4/CD8 ratio. These factors could successfully be skewed in vitro to enhance the potency and change the cell phenotype by delaying the addition of the blocking Ab. Despite the difference in approach, inhibitor- or antibody-based approaches generated NKR-2 CAR T cells with highly similar phenotypes and in vivo activity. Finally, even though it was not practical to inhibit all NKG2D ligands, inhibition of the two most important ligands through transient (shRNA) or permanent (Crispr/Cas) approaches also generated NKR-2 CAR T cells with highly similar phenotypes.

These results indicate that target-driven fratricide can be overcome using different approaches that can enable the development of T cell therapies where self-expression of the target ligand is a limiting factor.

Materials and Methods

Antibodies and Flow Cytometry

Cells were stained with fluorochrome labeled CD3 (BD, 345766), CD4 (BD, 345809), CD8 (BD, 345772), CD314 (BD, 558071), CD45RA (BD, 550855), CD62L (BD, 555544), CD279 (eBioscience, 12-2799-42), CD19 (BD, 345791, CD223 (eBioscience, 25-2239-41), MICA/B (R&D Systems, FAB13001G-100), MICB (R&D Systems, FAB1599G), ULBP1 (R&D Systems, FAB1380C), ULBP2/5/6 (R&D Systems, FAB1298A), ULBP3 (R&D Systems, FAB1517P), ULBP4 (R&D Systems: FAB6285A), and corresponding isotypes according to standard protocols. Briefly, cells were harvested and resuspended in a buffer containing DPBS (Life Technologies, A1285801) supplemented with 5% human serum albumin (Octapharma, 68209-633-02) and 0.01% NaN3 (Sigma, S2002). Cells were incubated with antibodies for 30 min at 4° C., washed with PBS and analyzed on a Guava easyCyte 6HT cytometer (Millipore). Antibodies were all titrated prior to experimental use. Viable cells were selected based on FSC/SSC. In all instances, an unlabeled control and an isotype control were used. Analysis was performed using Flowio v10.

Plasmids and Vector Production

Chimeric NKG2D (chNKG2D) construct was made as previously described (Zhang, Barber, & Sentman, 2006) and cloned into the Mo-MLV-based oncoretroviral vector SFG between NcoI and XhoI restriction sites. The pSFG GFP plasmid and pSFG htCD19.1 (coding for a truncated form of human CD19 (tCD19)) were a kind gift from Celdara Medical LLC (Lebanon, N.H., USA). GP2-293 packaging cells were transiently transfected with the relevant plasmid together with VSV-G envelop plasmid. Retrovirus suspensions produced in PG2-293 cells were used to spin-transduce PG13 cells to obtain stable producer cell lines. Vector particles used to transduce human T lymphocytes were harvested from PG13 stable producer cells after the culture reached confluence. Vector titers were measured using the Retro-XTM qRT-PCR Titration Kit (Life Technologies, CL 631453).

NKG2D-CAR T Cell Production

Peripheral blood mononuclear cells (PBMC) were isolated from whole blood of healthy donors (ImmuneHealth, CHU, Tivoli) by ficoll density gradient (VWR, 17-5442-03) according to standard procedures. Briefly, whole blood was diluted three times with DPBS and added carefully onto the ficoll layer in a 50 ml tube. Tubes were centrifuged at 500 g and the intermediate layer carefully removed. The PBMCs were subsequently washed three times with DPBS, harvested and subsequently activated in X-Vivo 15 medium (Westburg, BE02-0610) containing 5% of human sera (Access Biologicals, 515-HI) and supplemented with 40 ng/ml OKT3 (Miltenyi, 170-076-124) and 100 IU/ml IL-2 (Miltenyi, 170-076-146). Cells were incubated for two days in an incubator maintained at 37° C., 5% CO2. Cells were subsequently harvested and transduced in 24-well ($1\times10^6$ cells/well) plates coated with 8 μg/ml retronectin (Life Technologies, T100B) with different viral vectors and incubated for 2 days. Cells were then harvested from the 24 well plates, washed with HBSS (Westburg, BE10-543F) and transferred to G-Rex containers (Wilson Wolf, 80040S) for the expansion phase for an additional 4 days in complete X-Vivo 15 containing serum and IL-2 or as described in the text. At the end of the expansion phase, cells were harvested and used accordingly.

Cell Lines and Culture Reagents

The chronic myeloid leukemia cancer cell line K562 and the pancreatic cancer cell line PANC-1 were purchased from ATCC and maintained in IMDM (Westburg, LO BE12-722F) or DMEM (Westburg, LO BE12-604F) respectively, containing 178 10% FBS (Gibco, 16140071) and 1% penicillin/streptomycin (ThermoFisher Scientific, 15140122) until the time of use. The PI3K inhibitor LY294002 was purchased from Selleck Chemicals (S1105). Inhibiting antibodies to NKG2D or corresponding isotypes were purchased from BioLegend (Inhibiting antibody (Ultraleaf CD314) clone: 1D11, ImTec Diagnostics NV, 320814).

Cytolytic Assay

Adherent PANC-1 cells were cultured for 20 hours in a flat-bottom 96-well plate in the presence or absence of thawed NKR-2 T cells or tCD19 transduced cells at a ratio of 1:1 in X-Vivo 15 without phenol red containing 5% human sera (HS). T cells were washed and remaining adhering PANC-1 cells were labelled for 4 hours with alamarBlue (ThermoFisher Scientific, DAL1025). Viable cells were measured using Fluorescence at 530 nm using a SpectraMax M2 (Molecular Devices) and the relative cytolytic activity calculated.

Cytokine Release Assay

Fresh NKR-2 T cells and/or control tCD19 cells were incubated with K562 or PANC-1 cells at a ratio of 1:1 in X-Vivo 15 containing 5% HS. Following an incubation of 24 h supernatants were harvested and IFN-γ measured by ELISA (R&D Systems, SIF50) according to manufacturer's protocol. As a positive control cells were activated with PMA (Sigma-Aldrich, P8139-5MG) and ionomycin (Sigma-Aldrich, 10634-1MG). To assess the background levels of activation the cells received no stimulus.

Antibody Inhibition Assay NKR-2 T cells were incubated with 1 μg/mL of NKG2D blocking antibody, isotype control or no antibody for 24 hours and subsequently NKR-2 T cells mediated secretion of IFN-γ measured. Similarly, NKR-2 cells were co-cultured with cancer cells in the presence of antibody and cytokine secretion measured.

RNA Extraction and qPCR

PBMCs were stimulated with 40 ng/mL OKT3 and IL-2 (100 IU/mL) for 2 days, transduced and cultured for two more days with 40 ng/mL OKT3 and IL-2 (100 IU/mL), then expanded in the presence of IL-2 (100 IU/mL) until day 8 or 10 as described in detail in the text. Total RNA was isolated every two days using the RNeasy Mini Kit (Qiagen, 74104). Quantitative PCR reactions were conducted using pre-designed TaqMan gene expression assays (Hs04187752_mH, Hs01026642_m1, Hs00607609_mH, Hs00906262_m1, Hs00741286_m1, Hs01584111_mH, Hs04194671_s1, Hs00360941_m1, ThermoFisher Scientific) for the NKG2D ligands and Light Cycler 480RNA master mix (Roche, 04991885001). Relative expression was based on the housekeeping gene cyclophilin using in house designed primers (5'-GACGGCGAGCCCTTGG-3' and 5'-GCACGAAAAT-TTTCTGCTGTCTT-3') and probe (5' TEX615-TCTCCTTTGAGCTGTTTGCAGACAAGGT-3' BHQ™). Results are presented as fold induction compared to day 0 (calculated as $2^{\wedge}-\Delta\Delta CT$). All gene expression assays were tested on different cancer cell lines known to express the ligands.

Animal Studies

All in vivo experiment were performed at Voxcan (Marcy l'Etoile-France). Briefly, NOD/scid IL2rgnull (NSG) mice were irradiated 24 hours prior tumor injection (day −1). At day 0, THP-1-luc-GFP cells were engrafted by IV injection of 200 μl of PBS containing $5 \times 10^6$ THP-luc-GFP cells/mice. On Day 7, THP-1-luc-GFP positive mice were divided into four treatment groups: (i) Control received an IV single injection of Vehicle (200 μl of HBSS); (ii) Mock tCD19 received a single IV injection of $10 \times 10^6$ Mock tCD19 T cells (200 μL); (iii) NKR-2 LY received a single injection of $10 \times 10^6$ NKR-2-LY T-cells (200 μl); (iv) NKR-2-optimized Ab received a single IV injection of $10 \times 10^6$ NKR-2-optimized antibody (200 μl). Tumor progression was evaluated by bioluminescence imaging on Day 4, Day 8, Day 15, Day 22, Day 28 and Day 35. Similarly, the body weight of each animal has been measured three times a week from Day-6.

Statistical Analysis

Where applicable an unpaired, paired two tailed t-test or non-parametric Mann-Whitney U test, was used to assess statistical significance. Statistical significance was considered when $p<0.05$.

Figure 2:
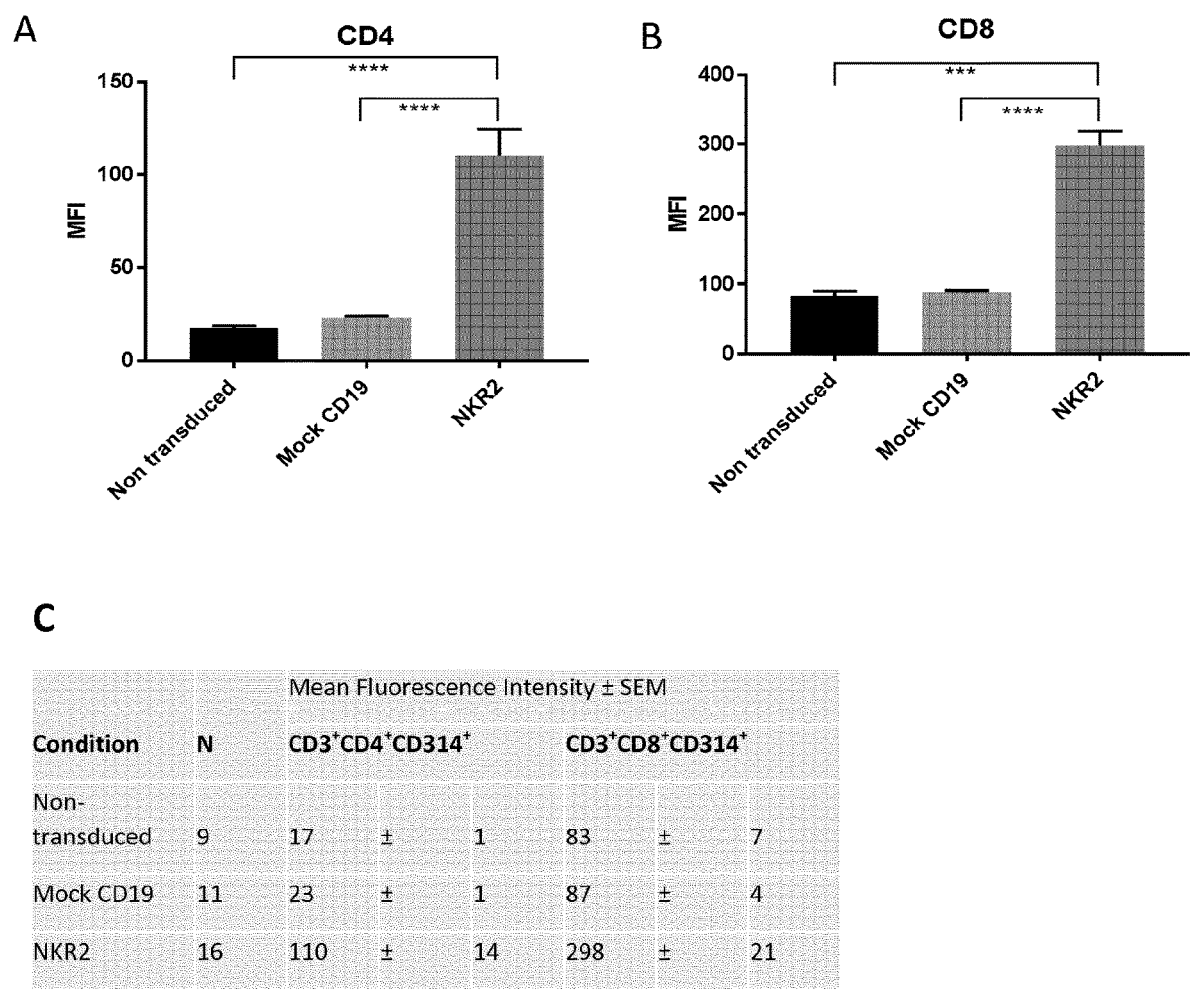
FIG. 2 Mean Fluorescence Intensity (MFI) of CD314. A-B) MFI of CD314 in $CD3^+CD4^+$ or in $CD3^+CD8^+$ T cells upon harvest of non-transduced, Mock CD19 transduced or NKR2 transduced T cells. Shown is the mean value of n=9 for non transduced, n=11 for Mock CD19 transduced and n=16 for NKR2 transduced T cells. A two-tailed unpaired t-test with Welch correction was used to assess significance (*P=0.0003. **P<0.0001). C) Mean fluorescence intensity values of non-transduced cells, Mock CD19 transduced or NKR2 transduced T cells from at least 9 different donors. Shown is the MFI and the standard error of the mean for both CD4 and CD8 T cells.

Example 1. NKR-2 CAR T Cells Undergo Fratricide that Drives the Phenotype and Expansion of the Engineered T Cell Population After transduction and in vitro culture, in the absence of methods to control fratricide, NKR-2 T cell populations display a predominantly CD8+ T cell subset composition as compared to T cells transduced with a control vector (truncated CD19 (tCD19), FIG. 1A). NKG2D expression is not exclusive to NKR-2 T cells but also clearly visible on control tCD19 T cells although engagement of the endogenous NKG2D fails to deliver a therapeutic response in the CAR T cell (32). However, the relative cell surface expression of NKG2D was highly increased in the NKR-2 T cell population indicative of transduction of the T cells with the CAR construct (FIG. 1B). The mean fluorescence intensity of NKG2D (CD314) was significantly higher in the NKR-2 T cell populations in both CD4+ and CD8+ subsets confirming expression of the CAR in both subsets (FIG. 2A-C).

Interestingly, the NKR-2 T cell population displayed a reduced relative frequency of naïve cells (as defined by CD45RA+ and CD62L+ cells double positive) and increased frequency of CD279 (PD-1) and CD223 (Lag-3) when compared to the tCD19 control T cell population suggestive of an increased effector cell phenotype (FIG. 1C-1D). NKR-2 T cells demonstrated high levels of target cell induced IFN-γ secretion (FIG. 3A) and cytolytic activity (FIG. 3B) upon co-culture with cancer cell lines confirming the functionality of NKR-2 T cells. However, the yield/fold expansion (FIG. 3C) and viability (data not shown) of NKR-2 T cells during the culture and upon harvest was consistently reduced as compared to the tCD19 control T cells.

NKG2D ligand expression has been documented in T cells during mitogenic activation (22) while it is known that Natural Killer cells can undergo fratricide as a consequence of NKG2D receptor engagement(23, 24). Together, this raised the question whether NKR-2 T cells were undergoing fratricide after transduction putatively driving low cell yield and viability, CD4/CD8 ratio bias and enhanced effector memory differentiation. To test this, T cells from a donor were transduced with an eGFP expression vector and mixed with NKR-2 T cells generated from the same donor to explore whether general T cell killing was occurring. Twenty-four hours later, there was a clear loss of eGFP T cells in the NKR-2 T cells co-culture implying targeted killing of autologous T cells by NKR-2 T cells (FIG. 3D).

Figure 3:
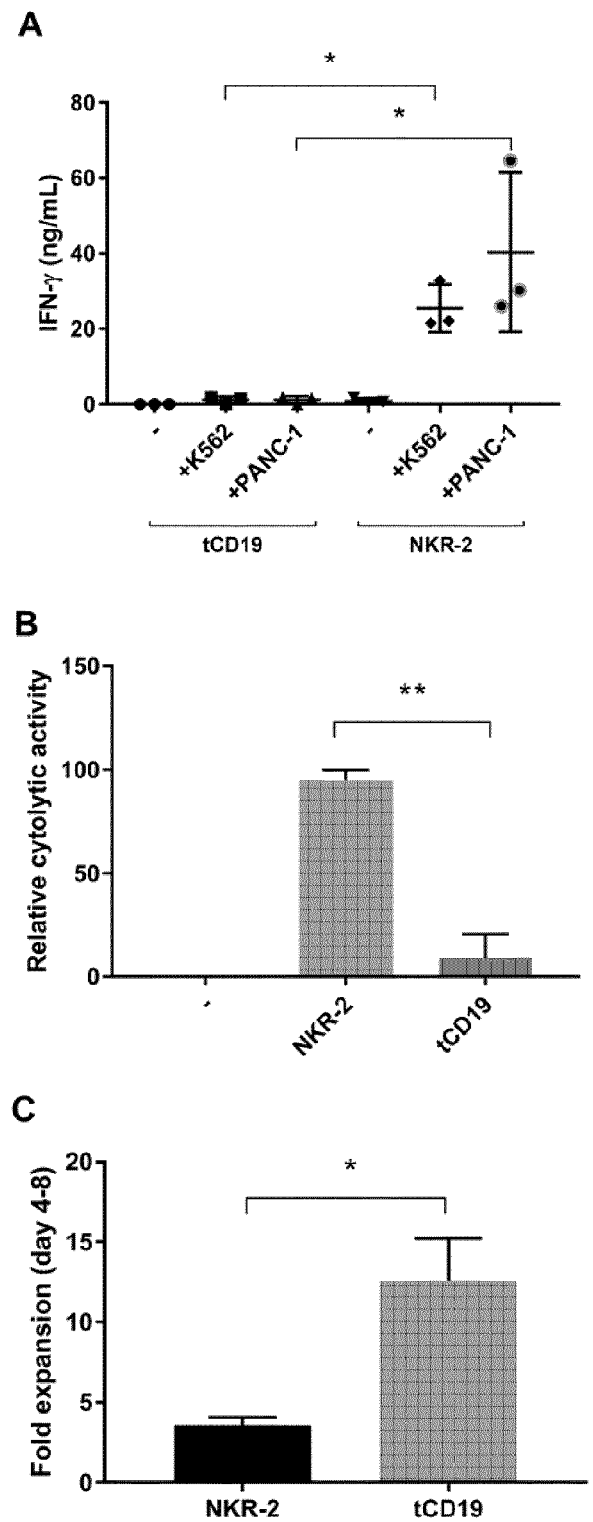
FIG. 3: NKR-2 T cells recognize Chronic myeloid leukemia (K562) and Pancreatic Carcinoma (PANC-1) but display a fratricide effect due to NKG2DL expression. (A) T cells from healthy donors were transduced with tCD19 vector (tCD19 T cells) or with the NKR-2 T cells vector (NKG2D-CAR T cells) and co-cultured with indicated cell lines or alone (−). IFN-γ secretion (ng/ml) was quantified by ELISA after overnight coculture. Each data point represents the mean value of duplicate wells from independent experiments. Shown is (N=3). (B) NKR-2 T cells exhibit cytolytic activity. PANC-1 were cocultured with thawed NKG2D-CAR T cells at an E:T ratio of 1:1. Alamar blue signal was determined after 20 hours. Percent lysis was determined by absorbance comparison with untreated cancer cells (PANC-1). Data shown are mean±SD of N=3 independent T cell donors; −: PANC-1 cells alone; NKR-2 T cells: Coculture of NKR-2 T cells and PANC-1 cells; tCD19: Coculture of control tCD19 T cells with PANC-1 cells. (C) Transduced T cells were cultured in complete X-vivo (100 IU/mL IL-2) for 4 days. T cells were analyzed 96 hours after seeding to analyze fold expansion relative to the initial cell seeding density. Data shown are mean±SD of N=3 independent T cell donors. (D) Representative co-culture experiment (out of three). GFP positive T cells were either cultured alone (Mock-GFP) or cocultured with NKR-2 T cells generated from the same donor (Mock GFP+NKR-2 T cells). Flow cytometry analysis of GFP positivity was acquired at the beginning of the incubation (T=0 h) or after 24 hours of incubation (T=24 h). (E-F) PBMCs were activated with 40 ng/mL anti-CD3 and 100 IU/mL IL-2 and kept in culture for a total of 8 days in accordance with the normal manufacturing protocol. Every 2 days cell samples were harvested and the expression of NKG2D ligands analyzed as either RNA (E) or proteins on the cell surface (F). A two-tailed unpaired t-test was used to assess statistical significance. A p<0.05 was considered significant (*) and p<0.01 (**). For both qPCR and Flow cytometric comparison a paired two-tailed t-test was used.
Figure 3:
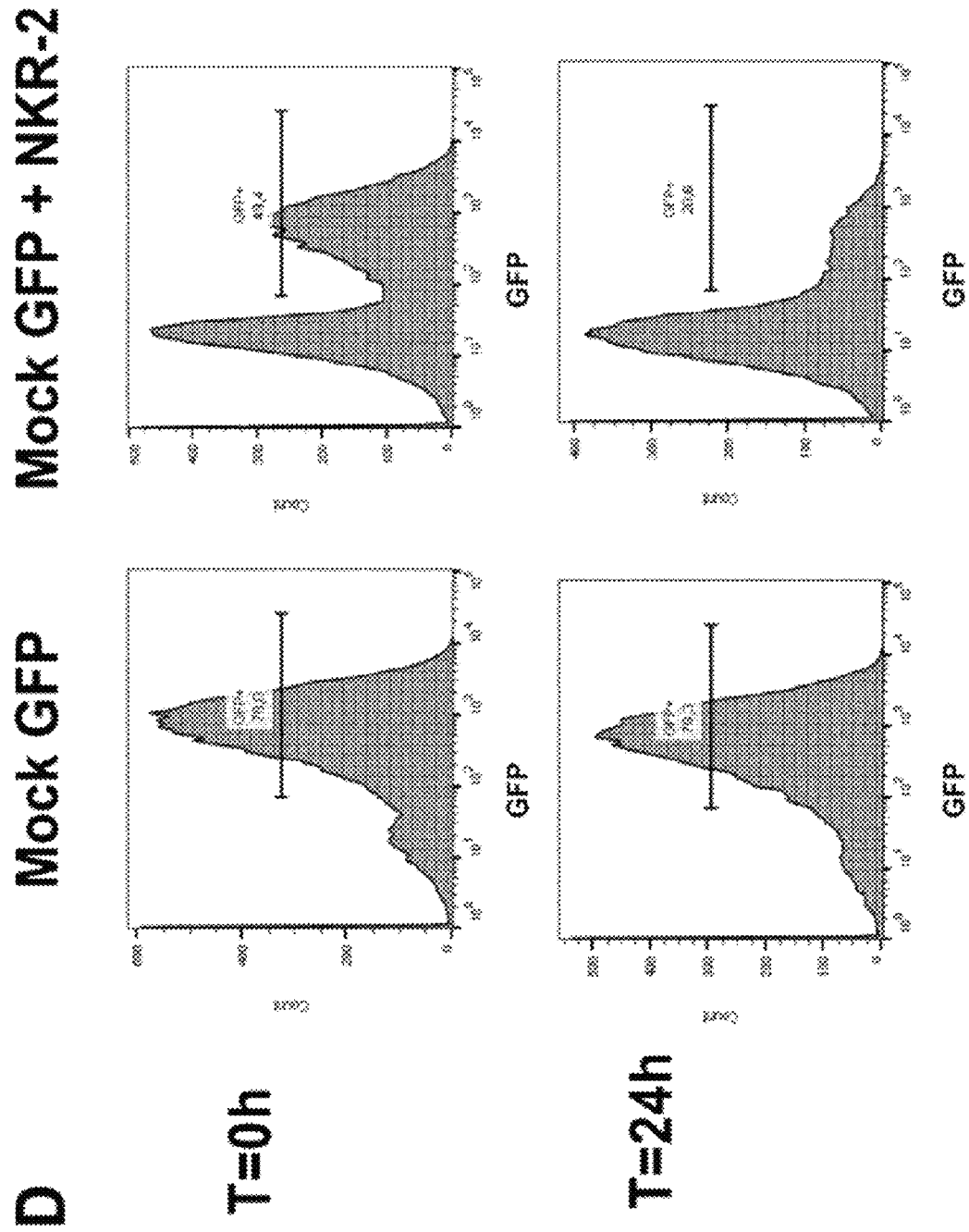
Figure 3:
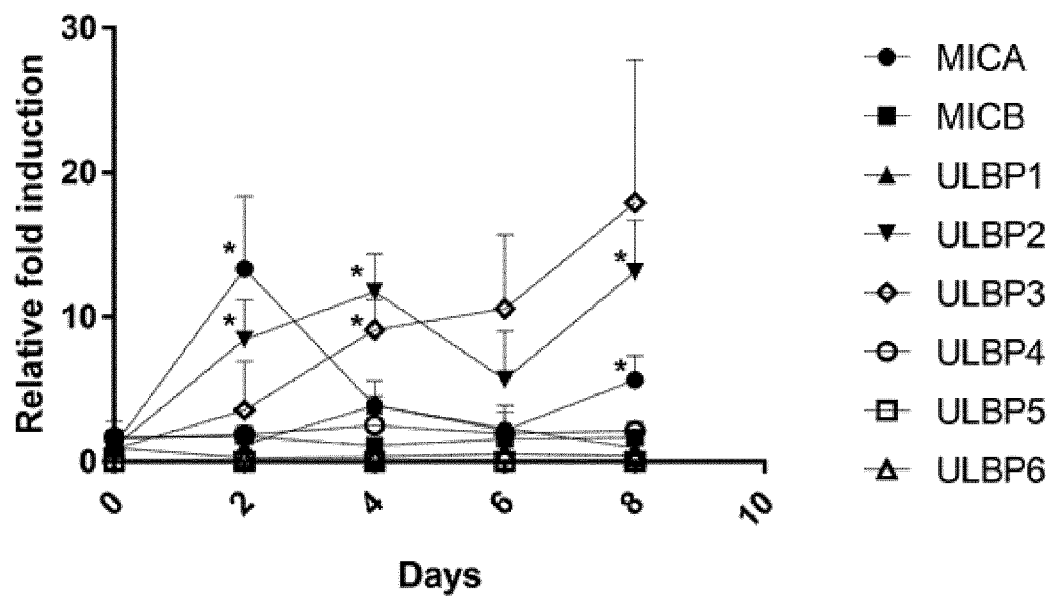
Figure 3:
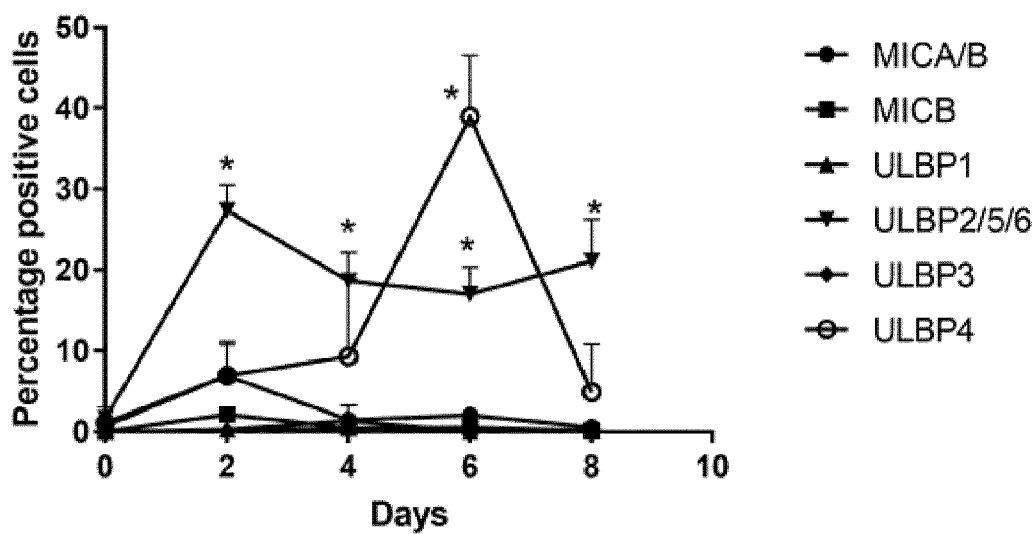

To understand the NKG2D ligand expression profile in activated T cells, three healthy donors were used as a source of T cells for activation without transduction and qPCR analysis was performed to examine the kinetics of NKG2D ligand mRNA expression profile (FIG. 3E). A rapid increase in MICA and ULBP2 mRNA levels was detected within two days of T cell activation. However, while the level of ULBP2 mRNA remained high, MICA was quickly reduced to the baseline within a further two days. The mRNA for ULBP3 increased gradually over the time-course while there was no relative increase in transcripts for MICB, ULBP5, ULBP1 nor ULBP6. Conversely, ULBP4 mRNA was slightly increased at day 4 but then reduced again to basal level. At the cell surface protein level, MICA/B followed a similar expression pattern to the corresponding mRNA, with a transient presence of MICA on day 2, that subsequently diminished (FIG. 3F). Unfortunately, no suitable antibodies were available to detect the individual ULBP2/5 and 6 proteins; however, the immune-reactivity observed with the antibody that recognizes all three family members was most likely due to ULBP2 based upon mRNA expression profile, which was the only one increased after day 2. Whilst highly induced at the mRNA 295 level, no cell surface ULBP3 could be detected. ULBP4+ cells reached a peak of positivity by day 6 before dropping back to baseline by day 8 following the pattern of mRNA expression with a two days delay (FIG. 3F). These observations were reflected in a parallel kinetics of mean fluorescence intensity (Table 1).

TABLE 1

Mean Fluorescence intensity (MFI) of all ligands of three different donors and their corresponding SD, following manufacturing process (samples were analyzed at day 0, 2, 4, 6 and 8).

| | Mean Fluoresence Intensity ± SD | | | | | |
|---|---|---|---|---|---|---|
| Day | MICA/MICB | MICB | ULBP1 | ULBP2/5/6 | ULBP3 | ULBP4 |
| 0 | 17.5 ± 0.8 | 8.4 ± 1.2 | 11.9 ± 0.5 | 15.9 ± 1.8 | 18.0 ± 0.1 | 19.0 ± 0.4 |
| 2 | 22.0 ± 4.8 | 13.5 ± 0.5 | 14.4 ± 0.3 | 24.7 ± 0.8 | 21.6 ± 1.2 | 29.7 ± 6.0 |
| 4 | 24.9 ± 2.9 | 14.9 ± 1.5 | 15.8 ± 1.2 | 28.6 ± 2.5 | 24.3 ± 1.5 | 36.9 ± 13.6 |
| 6 | 27.5 ± 1.2 | 12.8 ± 2.2 | 14.9 ± 0.2 | 27.8 ± 1.6 | 28.1 ± 1.3 | 80.3 ± 16.9 |
| 8 | 25.0 ± 1.4 | 14.9 ± 0.4 | 15.8 ± 0.3 | 28.1 ± 1.8 | 24.6 ± 0.7 | 28.9 ± 2.0 |

Together, these data imply that T cells modulate expression of NKG2D ligands after mitogenic activation with MICA, ULBP4 and putatively ULBP2 being the NKG2D ligands that predominate at the protein level albeit with differing kinetics of expression.

Example 2. PI3K Inhibition Improves NKR-2 T Cell Viability Upon Cryopreservation and Drives Increased NKR-2 Antigen-Specific Cytokine Production and Increased Memory Phenotype Upon ligand engagement, NKG2D and its associated DAP10 initiate signal transduction through the PI3K pathway in a manner similar to that of CD28 (25, 26). Therefore, we questioned whether inhibition of PI3K signaling could abrogate NKR-2 mediated fratricide during T cell culture. To this end, increasing concentrations of LY294002 were added (as a broad PI3K inhibitor) to the transduction and expansion phases of NKR-2 production.

Figure 4:
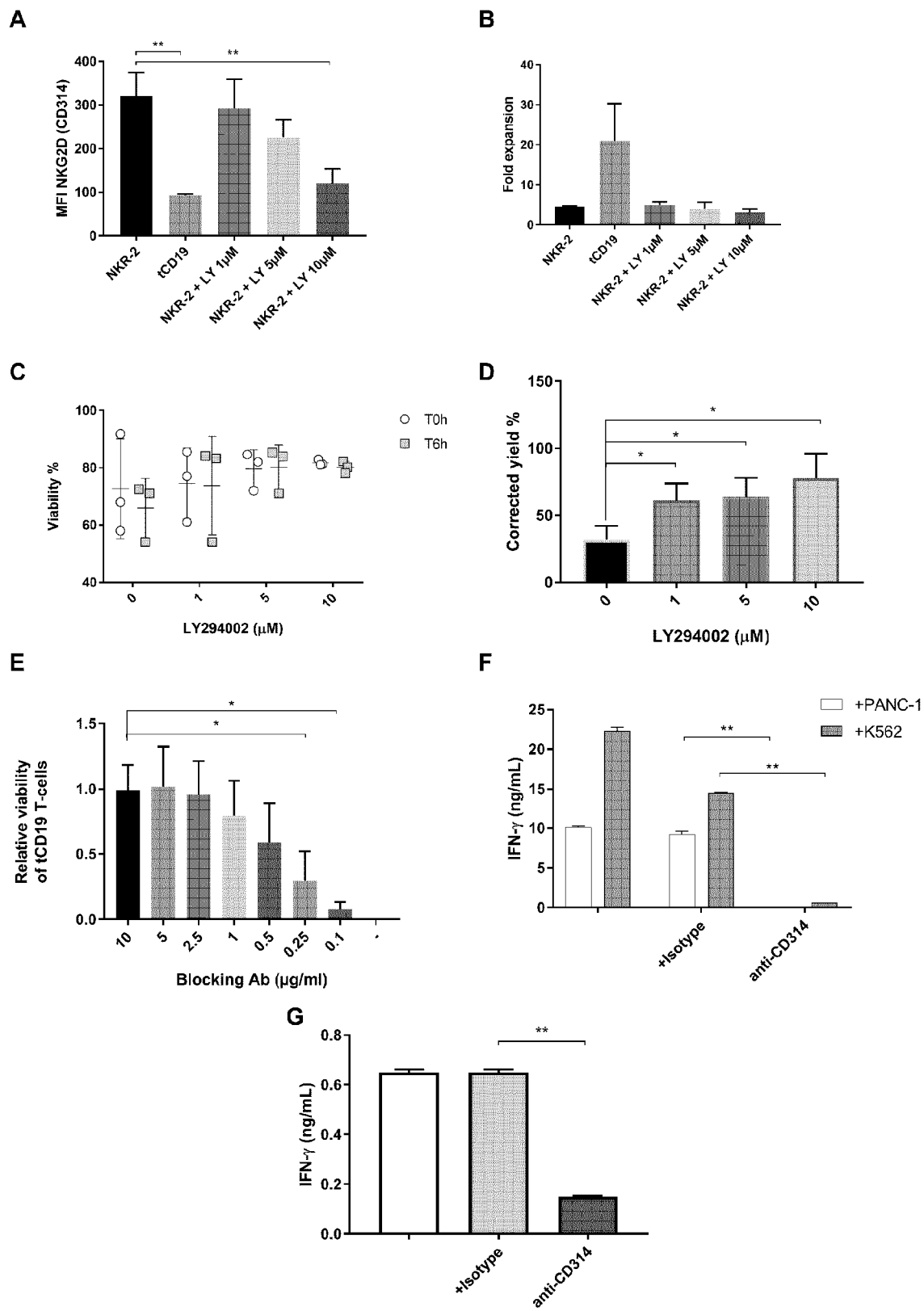
FIG. 4: NKR-2 T cells exhibit NKG2D mediated fratricide which can be inhibited by NKG2D blocking antibodies or PI3K inhibitor. (A) MFI of NKG2D expression on NKR-2 T cells treated or not with increasing concentrations of LY294002. Data shown are mean±SD of N=3 independent donors. (B) Transduced T cells were cultured in complete X-vivo (100 IU/ml IL-2) supplemented or not with increasing concentrations of LY294002 for expansion. T cells were analyzed 96 h after seeding for fold expansion relative to the initial cell seeding density. Data shown are mean±SD of N=3 independent donors. (C) Viability of cells after cryopreservation. NKR-2 T cells were produced in presence of increasing concentration of LY294002. After production, cells were harvested, washed, and formulate for cryopreservation. After cryopreservation, cells were thawed using a water bath and resuspended in Plasmalyte/Human Serum Albumin (HSA) 5%. Cells viability was directly assessed after thawing (T0 h) or after 6 hours at 4° C. in Plasmalyte/HSA5% (T6 h) (N=715 3) (D) NKR-2 T cells were produced in presence of increasing concentration of LY294002. After production, cells were harvested, washed, transferred in Plasmalyte/HSA1% (50×106 NKR-2 T cells/ml) and stored at 4° C. for 48 hours. After 48 hours, cell viability was assessed using trypan blue staining (N=3) and normalized for the number of cells at cryopreservation (E) tCD19 T cells were co-cultured with NKR-2 T cells generated from the same donor in presence of increasing concentrations of blocking Ab (from 0 (−) to 10 μg/ml). Flow cytometry analysis of CD19 positivity and viability was acquired after 44 hours of incubation. Data are normalized with CD19 positivity of Mock cultured without NKR-2 T cells (N=3). (F) Thawed NKR-2 T cells were cocultured with either PANC-1 cells or K562 cells at a 1:1 ratio, in the presence of CD314 blocking Ab, an isotype control or no Ab. Following a 24 h incubation, supernatants were harvested and IFN-γ measured (N=3). (G) Thawed NKR-2 T cells were left in culture for 24 h in the presence of an isotype control, the CD314 blocking Ab (or no Ab) and IFN-γ levels measured. Data shown are mean±SD of N=3 independent donors. A two-tailed unpaired t-test was used to assess statistical significance. A p<0.05 was considered significant (*) and p<0.01 (**).
Figure 5:
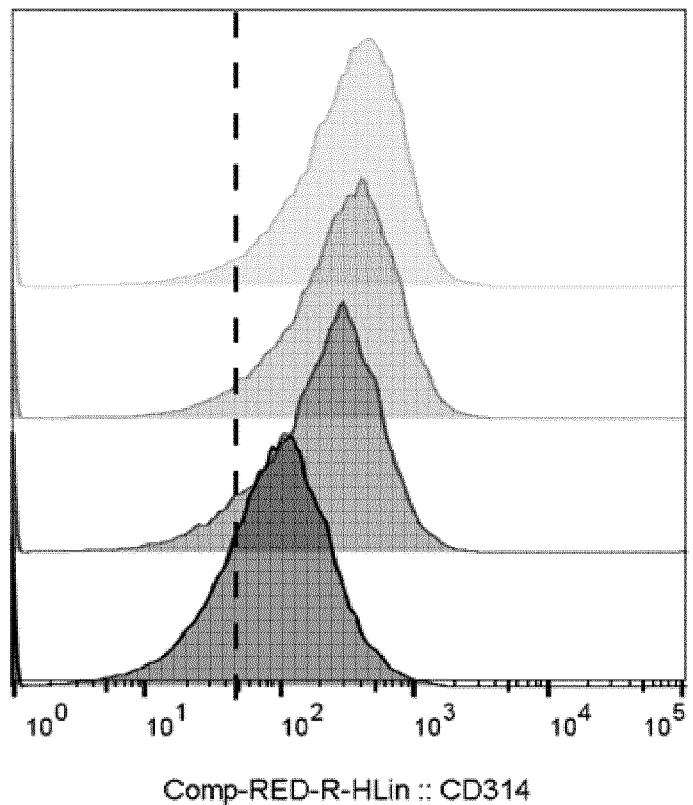
FIG. 5: MFI of NKG2D expression on NKR-2 T cells treated or not with increasing concentrations of LY294002.
Figure 6:
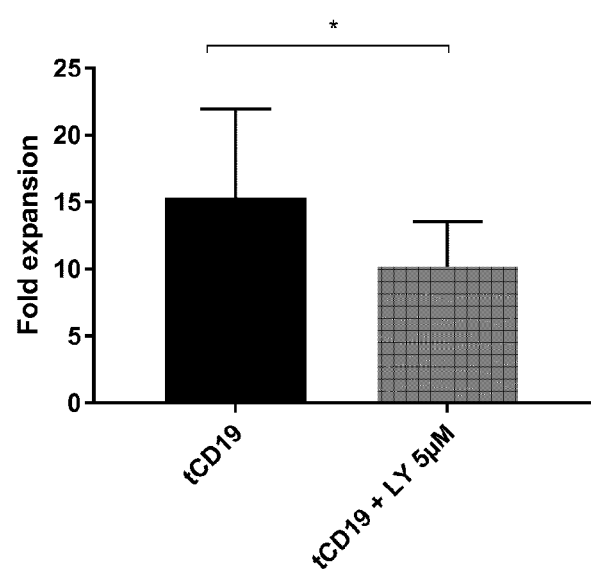
FIG. 6: fold expansion of tCD19 cells with or without presence of PI3K inhibitor

The addition of LY294002 resulted in several observations. Firstly, the cell surface expression of NKG2D on NKR-2 T cells was reduced in a dose-dependent manner, reaching the level of control tCD19 T cells at 10 μM (FIG. 4A and FIG. 5). This reduction was furthermore reversible as removal of LY from the culture led to an increase in NKG2D expression up to the levels of untreated NKR-2 T cells (data not shown). However, there was no discernable improvement in cell yield with the inhibitor suggesting that fratricide during culture was either not being managed completely or that the PI3K inhibitor had a deleterious effect on proliferation (FIG. 3B). To assess whether LY294002 had an anti-proliferative effect, control tCD19 T cells were treated with the PI3K inhibitor during the culture. A clear reduction in the proliferative capacity of these control T cells was observed when compared to untreated tCD19 cells (FIG. 6).

Figure 7:
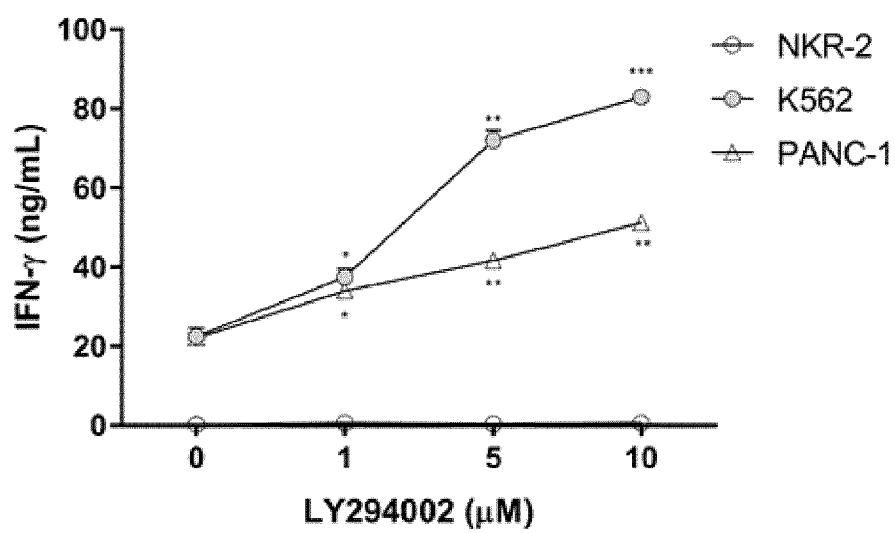
FIG. 7: NKR-2 T cells produced using PI3K inhibitor produced greater quantities of IFN-γ (A) and show increase memory phenotype (B)
Figure 7:
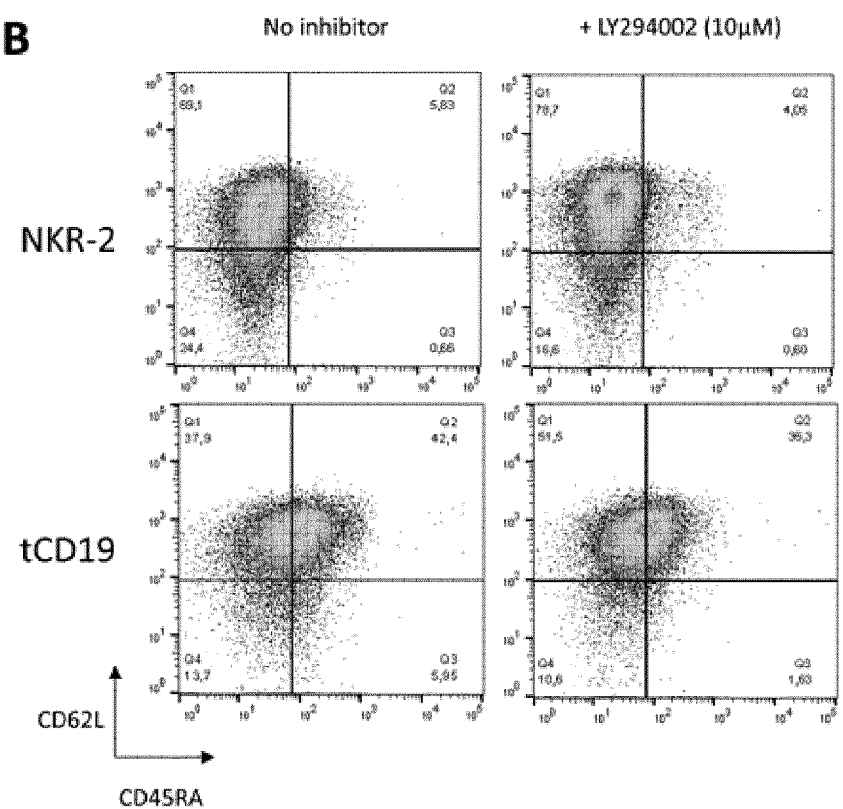

As expected, NKR-2 T cells manufactured with PI3K inhibitor showed an increase in cell viability both after cryopreservation or when stored at 4° C. for 48 hours (FIG. 3C, 3D). NKR-2 T cells produced using PI3K inhibitor produced greater quantities of IFN-γ in an LY294002 dose-dependent manner (FIG. 7A). Finally, NKR-2 T cells cultured with LY294002 also appeared to have an increased CD62L+/CD45RA− phenotype (FIG. 7B) in agreement with previously published work using this inhibitor to modulate the memory phenotype of T cells (27,28).

Overall, the addition of the PI3K inhibitor had beneficial effects upon NKR-2 T cells viability that are putatively attractive for therapeutic application.

Figure 8:
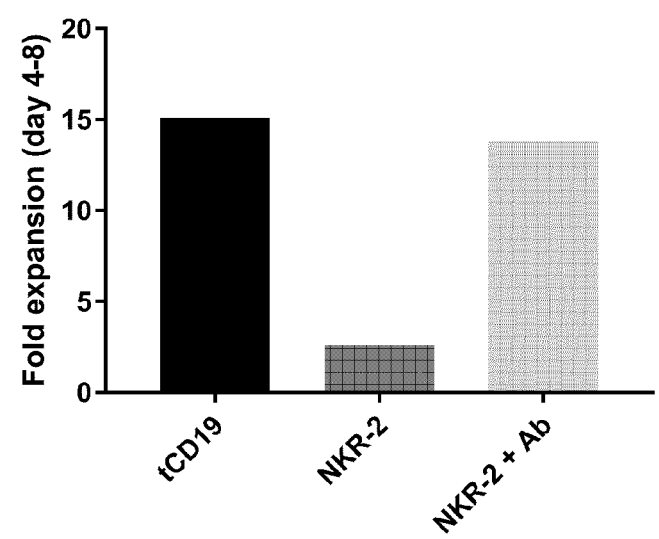
FIG. 8: fold expansion of NKR-2 T cells with and without antibody blockade

Example 3. Antibody Mediated NKG2D Blockade Prevents NKR-2 CAR T Cell Fratricide An initial experiment that included an anti-NKG2D antibody (clone 1D11) during the culture of NKR-2 T cells showed that NKR-2 T cell yield at the end of culture was equivalent to that of control T cells (2.6-fold expansion for NKR-2 T cells versus 13.8 fold expansion for NKR-2 T cells with antibody blockade (FIG. 8). This suggested that antibody blockade could abrogate NKG2D target-driven fratricide. A dose-titration experiment showed that antibody concentrations of 2.5 μg/mL and above resulted in protection of tCD19 T cells 358 from NKR-2 T cell targeted killing (FIG. 4E). The anti-NKG2D antibody also effectively blocked IFN-γ release completely during target cell engagement (FIG. 4F) thereby confirming the specificity of the NKR-2 T cells. The effective blocking of fratricide using the anti-NKG2D antibody was further supported by the fact that the IFN-γ release observed during the NKR-2 T cell production, putatively due to T cell fratricide, was significantly reduced by the addition of the blocking antibody (FIG. 4G). Since the mouse blocking antibody could potentially cause toxicities by antibody-dependent cell-mediated cytotoxicity (ADCC), extensive washing steps were realized after harvest. IgG ELISA and flow cytometry experiments indicated that no contaminating antibody could be detected in the supernatant or on the cell surface after harvest (data not shown). To assess ADCC, cocultures of NK cells with autologous NKR-2 cells in the presence of 5 μg/mL of Ab were conducted with no evidence of ADCC (data not shown). Together these data suggest that the addition of anti-NKG2D blocking antibody controlled NKR-2 T cells CAR driven fratricide.

Example 4. Antibody Mediated NKG2D Blockade and PI3K Inhibition of NKG2D Signaling are Functionally Equivalent in Manufacture of NKR-2 Expressing Cells Adaptation of Ab Blockade Process During In Vitro NKR-2 Cell Expansion Allows for Increased Yields with Equivalent Activity In Vitro and In Vivo.

Figure 9:
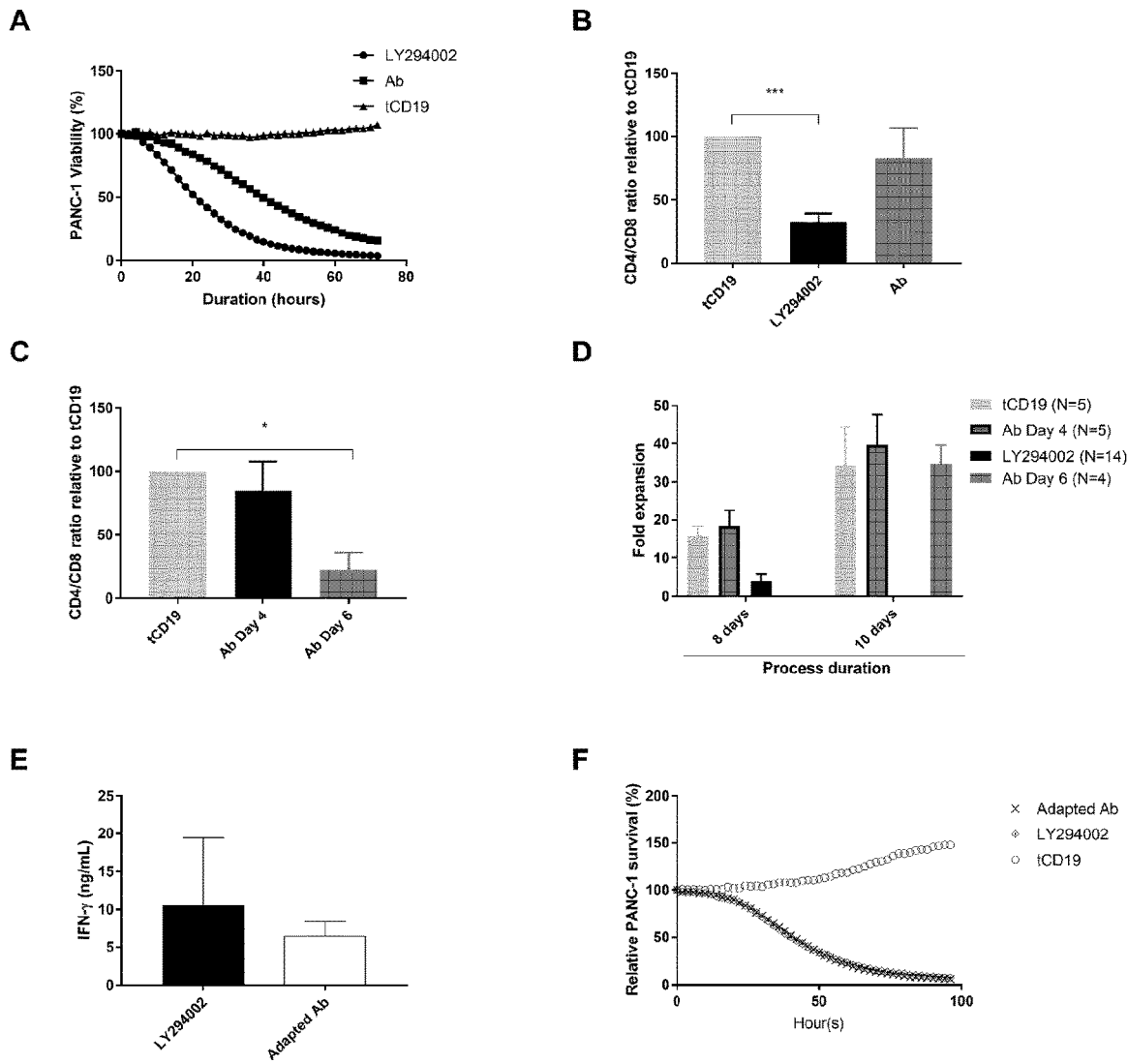
FIG. 9: NKR-2 T cells Ab blockade process adaptation restores CD4/CD8 ratio. (A) Cytolytic activity kinetics, one representative killing assay out of three. Thawed control tCD19 T cells or NKR-2 T cells treated with PI3K inhibitor LY294002 or with the blocking Ab were cultured in presence of NucLight positive PANC-1. PANC-1 viability was assessed every 2 hours by the IncuCyte S3 device. (B) CD4/CD8 distribution at harvest. During expansion phase, NKR-2 T cells were either cultured with 5 µM of LY294002 or with 5 µg/mL of blocking Ab for 96 hours, harvested and measured by Flow cytometry for the CD4 and CD8 population. Data shown are mean±SD of N=4 independent T cell donors relative to the control tCD19 ratio. (C) CD4/CD8 distribution at harvest with a delayed addition of blocking Ab. During expansion phase (day 4 to day 8), NKR-2 T cells were either directly treated with 5 µM of blocking Ab (day 4) or after 48 hours (day 6). At harvest (day 8), T cells were harvested and analyzed by Flow cytometry for the CD4 and CD8 populations. Data shown are mean±SD of N=3 independent T cell donors relative to control tCD19 CD4/CD8 ratio. (D) Comparison of expansion. NKR-2 T cells were either cultured for 8 days or 10 days in presence of LY or blocking Ab (added at day 4 or at day 6). T cells were analyzed at harvest for fold expansion relative to the initial cell seeding density. (E) Potency assay by IFN-γ secretion. Thawed NKR-2 T cells processed by the two methods were cocultured in presence of PANC-1 cells. IFN-γ secretion was measured by ELISA after 44 h of coculture. Data shown are mean±SD of N=4 independent T cell donors. (F) Cytolytic activity kinetics, one representative killing assay out of three. Thawed control tCD19 T cells or NKR-2 T cells treated with PI3Ki or with the blocking antibody were cultured in presence of NucLight positive PANC-1 cells. PANC-1 viability was assessed every 2 hours by the IncuCyte S3 device. A two-tailed unpaired t-test was used to assess statistical significance. A $p<0.05$ was considered significant (*), $p<0.01$ () and $p<0.001$ (*).

A comparison between NKR-2 T cells produced using the antibody and PI3K inhibitor processes showed different cytolytic kinetics, implying a change in T cell characteristics with the Ab process (FIG. 9A). In comparing the two processes the main difference observed was the CD4/CD8 ratio that, on day 8, was consistently skewed towards a CD8 population when the PI3K inhibitor was added. Interestingly, blocking of NKR-2 T cells rescued the CD4+ population, suggesting that the skewed CD4/CD8 ratio observed is fratricide dependent (FIG. 9B). The most likely explanation for the difference in ratio is either a relative increase in the ratio due to proliferation of the CD4 T cells, or a removal of the CD4 T cells by the CD8 T cells.

We hypothesized that the augmented lytic activity of NKR-2 T cells produced with the PI3K inhibitor could be due to the lower CD4/CD8 ratio. To address this, we adapted the blocking antibody process by adding the blocking antibody on day 6 instead of immediately following transduction (day 4). This modification led to the production of NKR-2 T cells exhibiting a CD4/CD8 ratio similar to that of the cells produced with the PI3K inhibitor (FIG. 9C), while maintaining a fold expansion comparable to control T cells (FIG. 9D). Subsequently, despite minor differences in certain parameters between the two processes such as the expression of the activation marker CD25 and the memory phenotype (data not shown), functional cytokine secretion and cytolytic activity of NKR-2 T cells against target cancer cells was comparable between both processes (FIG. 9E, F).

In a preliminary in vivo experiment using NOD SCID gamma mice receiving LY and Ab process generated NKR-2 cells showed a similar anti-tumor activity in an established acute myeloid leukemia (THP-1) tumor model (8 days post infusion as visualized by bioluminescence; tCD19: 5.76E10+/−4.46E10; NKR-2 LY: 7.15E08+/−1.01E09; NKR-2 Ab: 6.43E08+/−1.25E08; data not shown). A one way ANOVA with Tukey's post hoc test showed significant differences between LY and tCD19 control cells (p:0.02) and Ab produced NKR-2 compared to tCD19 (p=0.03). No difference was observed between LY and Ab groups (p=0.95). Additionally, a similar engraftment after twenty-four hours was observed in both NKR-2 LY and Ab group (LY group: 1.838+/−1.07%; Ab group: 1.792+/−0.56%; data not shown), indicating that no significant difference could be detected in short-term engraftment between the two groups.

Taken together, these combined data indicated that NKR-2 T cells produced with the adapted blocking antibody process exhibited a similar short-term engraftment and potency to the cells produced using the PI3K inhibitor.

Figure 10:
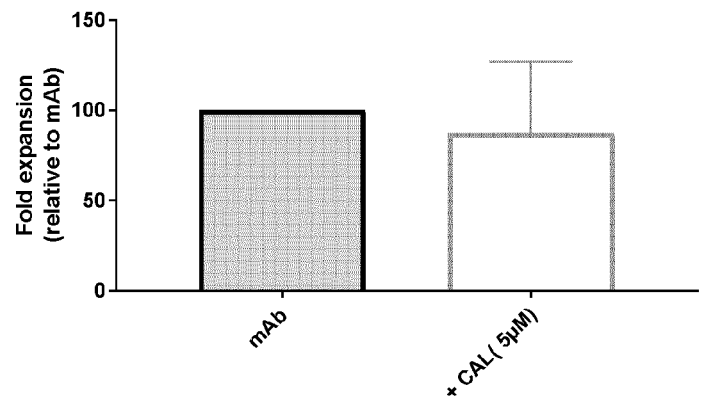
FIG. 10. Idelalisib (Cal101) vs NKG2D blocking antibody. Comparison of cell expansion (A), viability (B), and potency as measured by IFN gamma secretion post coculture with K562 cells (C) of cells cultured in the presence of the blocking NKG2D antibody or 5 µM CAL101.
Figure 10:
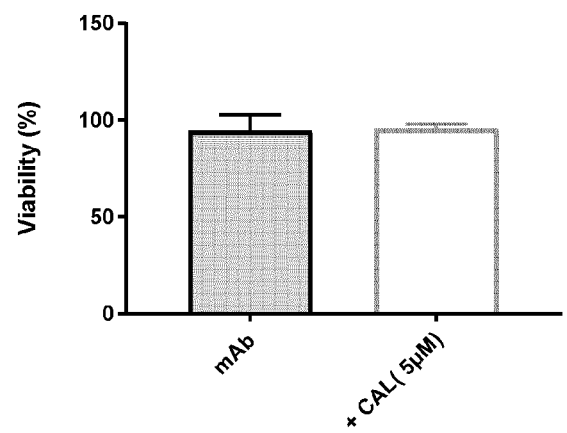
Figure 10:
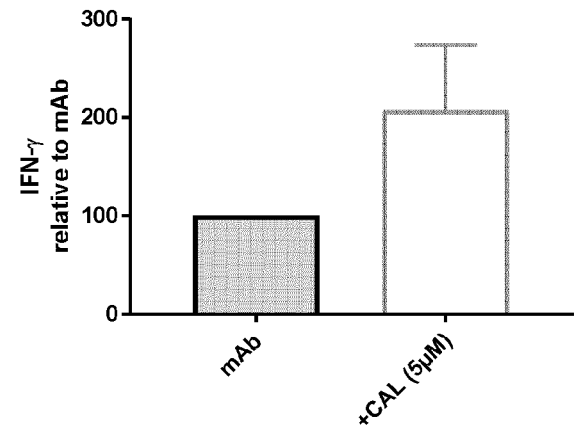

The Effect on NKR2 Manufacture is PI3K-Mediated, and not Due to the Specific Inhibitor To further confirm whether the effect of LY294002 was indeed linked to its PI3K inhibitory activity, several other PI3K inhibitors were tested, including wortmannin and CAL-101 (idelalisib). Representative data is shown for CAL-101 in FIG. 10. Cal-101 performs similar to the blocking antibody in terms of fold expansion (FIG. 10A) and cell viability (B). Like with other PI3K inhibitors, the cells seem to produce more interferon (FIG. 10C) which may contribute to higher potency. Downstream inhibitors of the PI3K pathway (such as the glycogen synthase kinase 3 beta inhibitor TWS119 or the mTOR inhibitor rapamycin) were also tested. The results obtained were similar (data not shown), in that expansion is increased compared to cells without inhibition of NKG2D signaling, although PI3K inhibition appears to result in cells with the most desirable properties. This may at least in part be due to the toxic properties of e.g. rapamycin.

Figure 11:
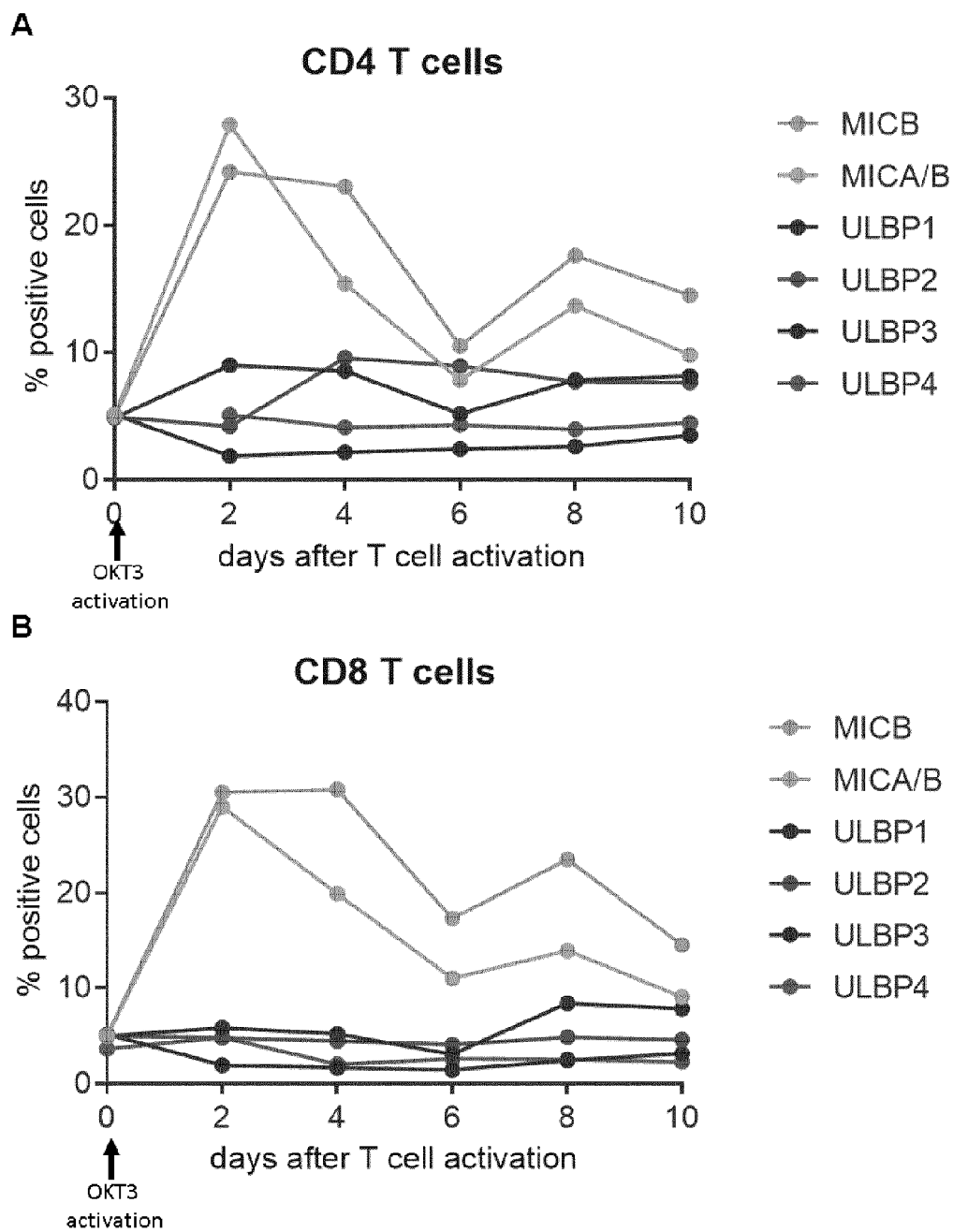
FIG. 11. Expression of NKG2D ligands on the surface of CD4+(A) and CD8+(B) T cells FIG. 12. Co-expression of MICA/B targeting shRNA reduces fratricide FIG. 13. Reducing fratricide increases killing of cancer cells.

Example 5. Inhibition of NKG2D Ligands Also Leads to Improved Cell Yield and Cytolytic Activity NKG2D is known to engage 8 different stress-induced ligands (NKG2DL) broadly present on tumors but largely absent on healthy tissues. We aimed to identify the key NKG2DL expressed on T cells upon activation. PBMCs were activated at day 0 with OKT3 and anti-CD3 antibody. The expression of the eight NKG2DL was assessed every other day on the surface of CD4+ and CD8+ T cells (FIG. 11). Upon activation, MICA/B and MICB were upregulated on the cell surface of CD4 and CD8 T cells, with expression peaking at day 2-4 after activation. Subsequently, expression declined until day 10. ULBP1 and ULBP2 were expressed at low levels, whereas ULBP2 was restricted to CD4+ T cells (FIG. 11). There was little evidence of expression of the other ligands on T cells.

Parallel studies identified MICA and MICB as the major stimulators of the NKG2D CAR (data not shown), leading us to pose that MICA and MICB were the main NKG2DL responsible for fratricide of T cells.

Figure 12:
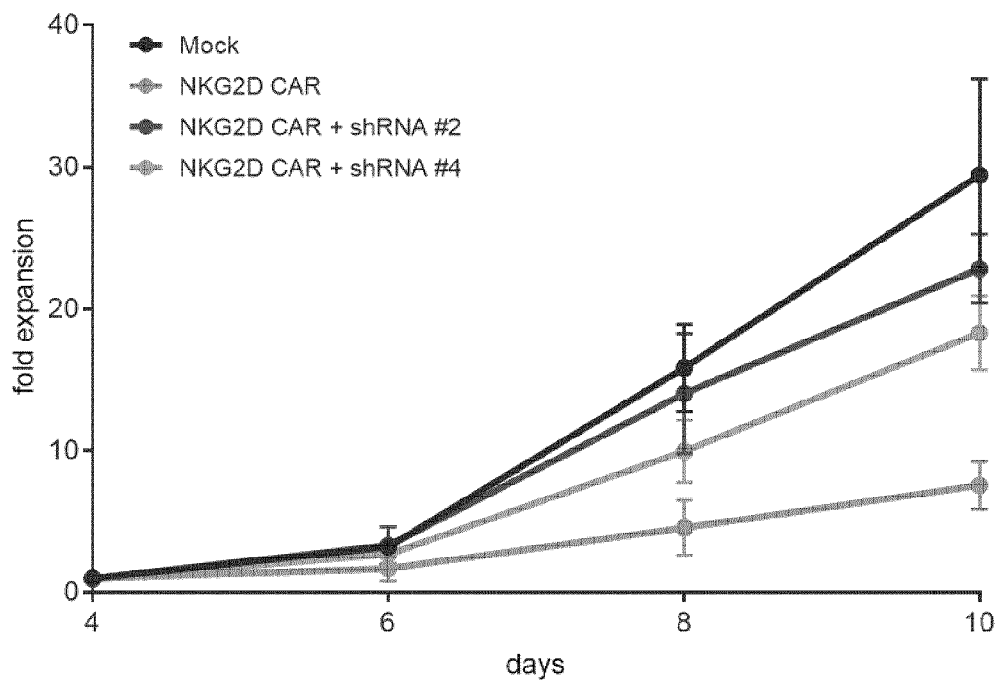
Figure 13:
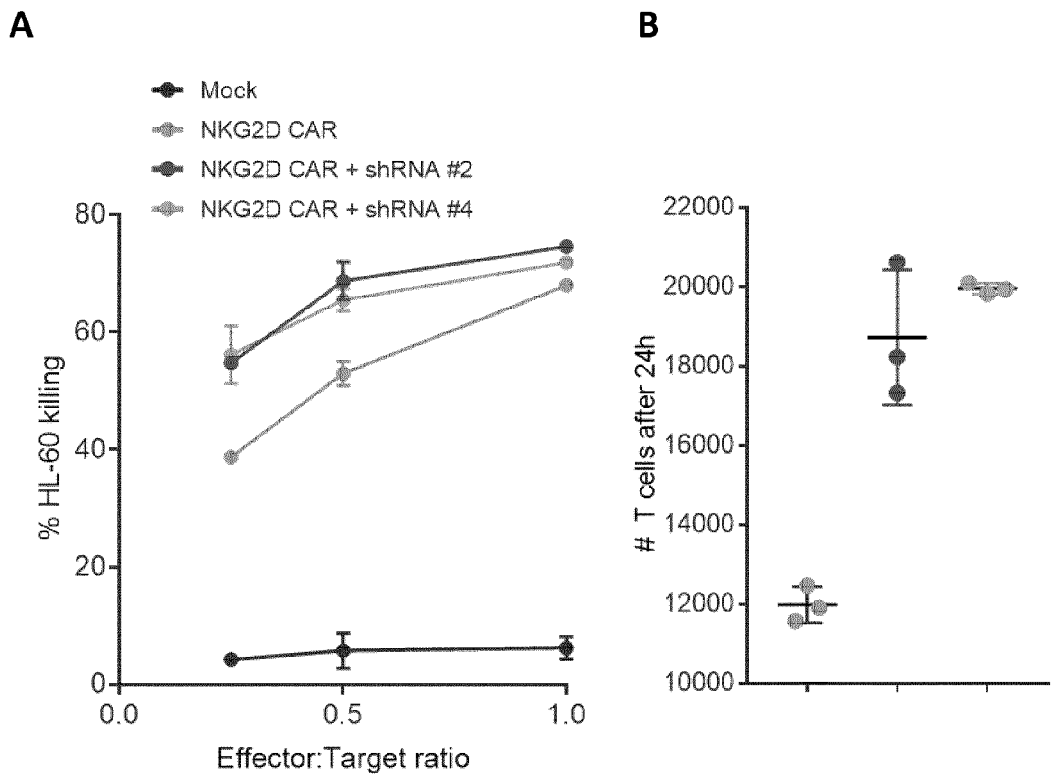

We then explored specific targeting of both MICA and MICB with a single shRNA, feasible since there is a high sequence similarity. Primary T cells were transduced with the different shRNAs and MICA and MICB protein expression was assessed. This screen identified two shRNAs to reduce cell surface expression of MICA and MICB (data not shown). Next, we engineered a single retroviral vector encoding the NKG2D CAR and coexpressing the candidate shRNA. We assessed the levels of fratricide in T cells engineered with NKG2D based CAR or T cells co-expressing a shRNA, by means of cell expansion (FIG. 12). Engineering of a single retroviral vector encoding the NKG2D CAR and shRNA generated T cells that had much reduced in vitro fratricide (FIG. 12), compared to cells without the shRNA and enhanced the rate of expansion of NKG2D CAR T cells approaching that of control T cells. Subsequently, we assessed the in vitro anti-tumor efficacy of NKG2D based CAR T cells with and without MICA/B-targeting shRNAs. Cells lacking the shRNA showed specific killing of AML HL-60 cells at the different effector to target (E:T) ratios. However, co-expression of MICA/B shRNA #2 or #4 improved killing of cancer cells, especially at lower E:T ratios (FIG. 13A). Improved target cell killing was likely due to decreased fratricide as shRNA expression improved T cell recovery 24 h after co-culture (FIG. 13B).

In conclusion, knockdown of NKG2D ligands in the T cells shows the same improved manufacturing results as observed for NKG2D inhibition or PI3K inhibition.

Similar data were obtained when permanently inactivating MICA and MICB using Crispr/Cas (data not shown). One notable difference is that shRNA inhibition can be done in a transient manner (e.g. only during the manufacturing process), while genetic knockout (here using Crispr/Cas) is permanent. This may be desirable or not, depending on the context.

Discussion

The recent approval of CD19 CAR T cell therapy in B cell acute lymphoblastic leukemia (bALL) and diffuse large B cell lymphoma (DLBCL) provides a strong clinical validation of the approach and provides an impetus to develop CAR T cell therapy beyond CD19+ B malignancies. The choice of target is essential to the success of the therapy. To date, the identification of tumor exclusive antigens has been challenging. A recent bioinformatics study combining proteomic and genomic approaches in Acute Myeloid Leukemia (AML), showed that there was no tumor specific cell surface antigen, and that complex combinatorial targeting strategies may be required for antibody-based CAR T approaches to target AML (29). Consequently, most target antigens being tested at present are tumor associated antigens where expression of the target may also be present on normal, healthy cells. There are many examples including CD19 for B cell malignancies(3, 4), CD123 in AML(30), CD7 (14) and CEA in a range of solid tumors(31). However, in the case where the target antigen may be permanently or transiently expressed on a T cell, this creates problems since the CAR engineered T cell would then be likely to target itself and others in the cultures resulting in T cell fratricide, which practically translates into a reduced or indeed, zero, cell yield.

Gene editing now provides a clinically relevant method to prevent the expression of specific proteins thereby enabling the expansion of CAR T cells that would otherwise undergo fratricide such as CD7-specific CAR T cells(14). However, the multi-target specificity of the NKG2D based CAR means that, prima facie, gene editing to eliminate eight different proteins in the primary T cell along with efficiently expressing the CAR construct, while possible, is challenging to put in practice for clinical applications. Thus, other strategies are presented herein to avoid fratricide occurring during cell culture to enable the production and delivery of a NKG2D-focused CART cell therapy.

In these Examples, a PI3K inhibitor provided a generic approach to control fratricide by reducing the NKG2D expression on the cell surface. This is, to our knowledge, the first time that such observation is reported. The mechanisms responsible for the loss of cell surface NKG2D after PI3K inhibitor treatment is currently unknown. What is known is that NKG2D cell surface localization is mediated by its association with DAP10 (Upsahw et al. 2006). One hypothesis for loss of cell surface NKG2D could be that DAP10 is impacted by the PI3K inhibitor treatment (e.g. decreasing RNA levels, inhibiting transcription or even inhibition of post translational modifications such as glycosylation, which are required for the association of DAP10 with NKG2D (Park Y P et al., 2011, Blood)). These could ultimately result in the prevention of expression of the NKG2D-DAP10 complex on the cell surface and thus inhibition of fratricide. However, PI3K inhibition is also associated with reduced cell proliferation (Aagaard-Tillery K M, Jelinek D F. Phosphatidylinositol 3-kinase activation in normal human B lymphocytes. J Immunol. 1996; 156:4543-4554. 11. Fruman D A, Snapper S B, Yballe C M, et al. Impaired B cell development and proliferation in absence of phosphoinositide 3-kinase p85alpha. Science. 1999; 283:393-397. 12. Shi J, Cinek T, Truitt K E, Imboden J B. Wortmannin, a phosphatidylinositol 3-kinase inhibitor, blocks antigen-mediated, but not CD3 monoclonal antibody-induced, activation of murine CD4 T cells. J Immunol. 1997; 158:4688-4695. 13. Truitt K E, Shi J, Gibson S, Segal L G, Mills G B, Imboden J B. CD28 delivers costimulatory signals independently of its association with phosphatidylinositol 3-kinase. J Immunol. 1995; 155:4702-4710.) thus this inhibitor approach provides an effective solution to control T cell fratricide in the setting where relatively low doses of CAR T cells would be required, but is of more limited use when high number of cells are required.

An alternative approach to inhibit fratricide during the manufacturing of NKR-2 T cells, was the use of a specific blocking antibody during the expansion phase. This enabled the control of T cell fratricide and the expansion of T cells to levels equivalent to that of control tCD19 T cells. This method is strongly dependent on the antibody used, as it needs to block fratricide without inducing CAR activation itself (as shown in a much-reduced level of cytokine production during culture in the absence of target antigen). The addition of the specific blocking antibody provides a solution that enables the large-scale expansion of NKR-2 T cells.

A major concern relating to the blocking antibody process was the strong likelihood that the expanded NKR-2 CAR T cells would be decorated with antibody thereby leading to the likely rapid elimination of the cells upon infusion through antibody-dependent clearance mechanisms. However, analysis clearly indicated that the NKR-2 cells lacked anti-CD314 antibody coating with re-expression analysis suggesting that antibody binding appears to result in loss of NKG2D and NKR-2 CAR from the cell surface. Upon binding to target ligand, endogenous NKG2D has been shown to undergo rapid internalization as a mechanism to control NK cell activation. The observations made here suggest that in the context of the NKR-2, the CAR also appears to be internalized. From an adoptive T cell therapy standpoint, this is advantageous since there is no need to develop a specific process to remove the bound antibody.

In addition to the differences observed between processes and the impact of PI3K inhibitors, these pre-clinical data give for the first time the confirmation that NKR-2 is a potent therapy in an AML mice model. Moreover, these results are in accordance with other studies where the lack of preconditioning as well multiple injections of NKR-2 were criteria that led to tumour eradication and long-term survival of treated mice (Zhang et al. Cancer Res. 2007; 67(22):11029-36; Barber et al., Gene Ther. 2011; 18(5):509-16).

Further, although it was not deemed feasible or practical to knock down or knock out all NKG2D ligands, the inhibition through shRNA or CRISPR of the two most common ligands in T cells has been performed, achieving a similar improvement in manufacturing yield, indicating that even a partial inhibition of NKG2D signaling can already improve fratricide.

Taken together, this work indicates that T cell fratricide can be managed by generic methods (e.g. acting on downstream signaling) such as PI3K inhibition or by receptor-specific approaches such as a blocking antibody or elimination of receptor ligands. Particularly the PI3K inhibitor and blocking antibody approaches can be used to generate immune cell products with reduced levels of fratricide, and each offers potential advantages that can be used to generate T cell products where other means such as gene-editing to eliminate the target in the T cell population is challenging or not currently feasible or desirable.

REFERENCES

1. Fesnak A D, June C H, Levine B L (2016) Engineered T cells: the promise and challenges of cancer immunotherapy. Nat Rev Cancer. 16: 566-81. doi: 10.1038/nrc.2016.97
2. Brenner M K (2017) Next Steps in the CAR Journey of a Thousand Miles. Mol Ther. 25: 2226-7. doi: 10.1016/j.ymthe.2017.09.013
3. Davila M L, Brentjens R J (2016) CD19-Targeted CAR T cells as novel cancer immunotherapy for relapsed or refractory B-cell acute lymphoblastic leukemia. Clin Adv Hematol Oncol. 14: 802-8.
4. Kochenderfer J N, Somerville R P T, Lu T et al. (2017) Long-Duration Complete Remissions of Diffuse Large B Cell Lymphoma after Anti-CD19 Chimeric Antigen Receptor T Cell Therapy. Mol Ther. 25: 2245-53. doi: 10.1016/j.ymthe.2017.07.004
5. Park J H, Geyer M B, Brentjens R J (2016) CD19-targeted CAR T-cell therapeutics for hematologic malignancies: interpreting clinical outcomes to date. Blood. 127: 3312-20. doi: 10.1182/blood-2016-02-629063

6. Rossig C (2017) CAR T cell immunotherapy in hematology and beyond. Clin Immunol. doi: 10.1016/j.clim.2017.09.016
7. Turtle C J, Hay K A, Hanafi L A et al. (2017) Durable Molecular Remissions in Chronic Lymphocytic Leukemia Treated With CD19-Specific Chimeric Antigen Receptor-Modified T Cells After Failure of Ibrutinib. J Clin Oncol. 35: 3010-20. doi: 10.1200/JCO.2017.72.8519
8. Rezvani K, Rouce R, Liu E, Shpall E (2017) Engineering Natural Killer Cells for Cancer Immunotherapy. Mol Ther. 25: 1769-81. doi: 10.1016/j.ymthe.2017.06.012
9. Adair P R, Kim Y C, Zhang A H, Yoon J, Scott D W (2017) Human Tregs Made Antigen Specific by Gene Modification: The Power to Treat Autoimmunity and Antidrug Antibodies with Precision. Front Immunol. 8: 1117. doi: 10.3389/fimmu.2017.01117
10. Guest R D, Kirillova N, Mowbray S et al. (2014) Definition and application of good manufacturing process-compliant production of CEA-specific chimeric antigen receptor expressing T-cells for phase I/II clinical trial. Cancer Immunol Immunother. 63: 133-45. doi: 10.1007/s00262-013-1492-9
11. Levine B L, Miskin J, Wonnacott K, Keir C (2017) Global Manufacturing of CAR T Cell Therapy. Mol Ther Methods Clin Dev. 4: 92-101. doi: 10.1016/j.omtm.2016.12.006
12. Wang X, Riviere I (2016) Clinical manufacturing of CAR T cells: foundation of a promising therapy. Mol Ther Oncolytics. 3: 16015. doi: 10.1038/mto.2016.15
13. Callard R E, Stark J, Yates A J (2003) Fratricide: a mechanism for T memory-cell homeostasis. Trends Immunol. 24: 370-5.
14. Gomes-Silva D, Srinivasan M, Sharma S et al. (2017) CD7-edited T cells expressing a CD7-specific CAR for the therapy of T-cell malignancies. Blood. 130: 285-96. doi: 10.1182/blood-2017-01-761320
15. Mamonkin M, Rouce R H, Tashiro H, Brenner M K (2015) A T-cell-directed chimeric antigen receptor for the selective treatment of T-cell malignancies. Blood. 126: 983-92. doi: 10.1182/blood-2015-02-629527
16. Leisegang M, Wilde S, Spranger S, Milosevic S, Frankenberger B, Uckert W, Schendel D J (2010) MHC-restricted fratricide of human lymphocytes expressing survivin-specific transgenic T cell receptors. J Clin Invest. 120: 3869-77. doi: 10.1172/JCI43437
17. Schendel D J, Frankenberger B (2013) Limitations for TCR gene therapy by MHC-restricted fratricide and TCR-mediated hematopoietic stem cell toxicity. Oncoimmunology. 2: e22410. doi: 10.4161/onci.22410
18. Sentman C L, Meehan K R (2014) NKG2D CARs as cell therapy for cancer. Cancer J. 20: 156-9. doi: 10.1097/PPO.0000000000000029
19. Lanier L L (2015) NKG2D Receptor and Its Ligands in Host Defense. Cancer Immunol Res. 3: 575-82. doi: 10.1158/2326-6066.CIR-15-0098
20. Spear P, Wu M R, Sentman M L, Sentman C L (2013) NKG2D ligands as therapeutic targets. Cancer Immun. 13: 8.
21. Demoulin B, Cook W J, Murad J, Graber D J, Sentman M L, Lonez C, Gilham D E, Sentman C L, Agaugue S (2017) Exploiting natural killer group 2D receptors for CAR T-cell therapy. Future Oncol. 13: 1593-605. doi: 10.2217/fon-2017-0102
22. Molinero L L, Fuertes M B, Rabinovich G A, Fainboim L, Zwirner N W (2002) Activation-induced expression of MICA on T lymphocytes involves engagement of CD3 and CD28. J Leukoc Biol. 71: 791-7.
23. Madera S, Rapp M, Firth M A, Beilke J N, Lanier L L, Sun J C (2016) Type I IFN promotes NK cell expansion during viral infection by protecting NK cells against fratricide. J Exp Med. 213: 225-33. doi: 10.1084/jem.20150712
24. Nakamura K, Nakayama M, Kawano M, Amagai R, Ishii T, Harigae H, Ogasawara K (2013) Fratricide of natural killer cells dressed with tumor-derived NKG2D ligand. Proc Natl Acad Sci USA. 110: 9421-6. doi: 10.1073/pnas.1300140110
25. Smith-Garvin J E, Koretzky G A, Jordan M S (2009) T cell activation. Annu Rev Immunol. 27: 591-619. doi: 10.1146/annurev.immunol.021908.132706
26. Upshaw J L, Arneson L N, Schoon R A, Dick O, Billadeau D D, Leibson P J (2006) NKG2D-mediated signaling requires a DAP10-bound Grb2-Vav1 intermediate and phosphatidylinositol-3-kinase in human natural killer cells. Nat Immunol. 7: 524-32. doi: 10.1038/ni1325
27. Abu Eid R, Ahmad S, Lin Y et al. (2017) Enhanced Therapeutic Efficacy and Memory of Tumor-Specific CD8 T Cells by Ex Vivo PI3K-delta Inhibition. Cancer Res. 77: 4135-45. doi: 10.1158/0008-5472.CAN-16-1925
28. Perkins M R, Grande S, Hamel A et al. (2015) Manufacturing an Enhanced CAR T Cell Product By Inhibition of the PI3K/Akt Pathway During T Cell Expansion Results in Improved In Vivo Efficacy of Anti-BCMA CAR T Cells. Blood. 126: 1893.
29. Perna F, Berman S H, Soni R K, Mansilla-Soto J, Eyquem J, Hamieh M, Hendrickson R C, Brennan C W, Sadelain M (2017) Integrating Proteomics and Transcriptomics for Systematic Combinatorial Chimeric Antigen Receptor Therapy of AML. Cancer Cell. 32: 506-19 e5. doi: 10.1016/j.ccell.2017.09.004
30. Mardiros A, Dos Santos C, McDonald T et al. (2013) T cells expressing CD123-specific chimeric antigen receptors exhibit specific cytolytic effector functions and anti-tumor effects against human acute myeloid leukemia. Blood. 122: 3138-48. doi: 10.1182/blood-2012-12-474056
31. Thistlethwaite F C, Gilham D E, Guest R D et al. (2017) The clinical efficacy of first-generation carcinoembryonic antigen (CEACAM5)-specific CAR T cells is limited by poor persistence and transient pre-conditioning-dependent respiratory toxicity. Cancer Immunol Immunother. 66: 1425-36. doi: 10.1007/s00262-017-2034-7
32. Barber A, Sentman C L. NKG2D receptor regulates human effector T-cell cytokine production. Blood (2011) 117:6571-81. doi:10.1182/blood-2011-01-329417

The invention claimed is:

1. A method of reducing and/or preventing fratricide during the manufacturing of immune cells expressing a chimeric NKG2D receptor, wherein said chimeric NKG2D receptor comprises (i) a NKG2D receptor polypeptide that binds to at least one NKG2D ligand selected from MICA, MICB, ULBP1, ULBP2, ULBP3, ULBP4, ULBP5 and ULBP6 and (ii) a signaling moiety that transduces a signal in immune cells that express the chimeric NKG2D receptor, comprising effecting functional inhibition of NKG2D signaling during the manufacturing process of the cells, by one or more of the following:
   (i) contacting the immune cells expressing the chimeric NKG2D receptor during manufacturing with an antibody or small molecule that specifically binds to a Phosphoinositide 3-kinase (PI3K) polypeptide thereby inhibiting PI3K signaling;
   (ii) introducing into the immune cells express the chimeric NKG2D receptor during manufacturing at least one nucleic acid that specifically binds to a Phosphoinositide 3-kinase (PI3K) nucleic acid thereby inhibiting PI3K signaling;
(iii) contacting the immune cells expressing a chimeric NKG2D receptor during manufacturing with at least one antibody specific to the NKG2D receptor polypeptide comprised in the chimeric NKG2D receptor and/or with at least one antibody specific to a NKG2D ligand selected from MICA, MICB, ULBP1, ULBP2, ULBP3, ULBP4, ULBP5 and ULBP6; or
(iv) introducing into the immune cells during manufacturing at least one nucleic acid that specifically binds to the nucleic acid in the chimeric NKG2D receptor nucleic acid which encodes for said NKG2D receptor polypeptide or introducing at least one nucleic acid that specifically binds to a nucleic acid encoding a NKG2D ligand selected from MICA, MICB, ULBP1, ULBP2, ULBP3, ULBP4, ULBP5 and ULBP6, wherein the binding of said nucleic acid which specifically binds to said NKG2D receptor nucleic acid or to said NKG2D ligand nucleic acid downregulates the expression of the NKG2D receptor or said NKG2D ligand.

2. The method of claim 1, which results in at least one of
(i) permanent or transient inhibition of one or more of the NKG2D ligands of the immune cells;
(ii) transient inhibition of the chimeric NKG2D receptor; or
(iii) transient inhibition of downstream signaling of the chimeric NKG2D receptor.

3. The method of claim 2, wherein permanent inhibition of the one or more of the NKG2D ligands is achieved by genetic knockdown using at least one shRNA or siRNA that targets a nucleic acid encoding at least one of said NKG2D ligands.

4. The method of claim 2, wherein transient inhibition of PI3K signaling is effected by contacting the immune cells with an antibody or small molecule that binds to a Phosphoinositide 3-kinase (PI3K) polypeptide.

5. The method of claim 4, wherein the small molecule or antibody is selected from LY294002 and idelalisib.

6. The method of claim 1, wherein functional inhibition is achieved using one or more shRNAs or siRNAs or an antibody against the NKG2D receptor or against one or more of said NKG2D ligands.

7. The method of claim 1, wherein the immune cells comprise one or more of T cells, NK cells, NKT cells, stem cells and iPSCs.

8. An engineered immune cell comprising a nucleic acid molecule encoding a chimeric NKG2D receptor, wherein said chimeric NKG2D receptor comprises (i) a NKG2D receptor polypeptide that binds to at least one NKG2D ligand selected from MICA, MICB, ULBP1, ULBP2, ULBP3, ULBP4, ULBP5 and ULBP6 and (ii) a signaling moiety that transduces a signal in immune cells that express the chimeric NKG2D receptor, and
one or more shRNAs and/or siRNAs that specifically bind to a nucleic acid encoding said NKG2D receptor polypeptide and/or that specifically bind to a nucleic acid encoding a NKG2D ligand selected from MICA, MICB, ULBP1, ULBP2, ULBP3, ULBP4, ULBP5 and ULBP6, wherein said shRNAs and/or siRNAs downregulate the expression of the NKG2D receptor and/or said NKG2D ligands.

9. The engineered immune cell of claim 8, wherein the immune cells comprise at least one of T cells, NK cells, NKT cells, stem cells and iPSCs.

10. A composition of immune cells comprising a nucleic acid molecule encoding a chimeric NKG2D receptor, wherein said chimeric NKG2D receptor comprises (i) a NKG2D receptor polypeptide that binds to a NKG2D ligand selected from MICA, MICB, ULBP1, ULBP2, ULBP3, ULBP4, ULBP5 and ULBP6 and (ii) a signaling moiety that transduces a signal in the immune cell that expresses the chimeric NKG2D receptor, and wherein the cells further comprise:
one or more shRNAs or siRNAs directed against the nucleic acid encoding the NKG2D receptor comprised in the nucleic acid encoding the chimeric NKG2D receptor and/or one or more nucleic acids directed against at least one nucleic acid encoding a NKG2D ligand selected from MICA, MICB, ULBP1, ULBP2, ULBP3, ULBP4, ULBP5 and ULBP6;
and/or the composition further comprises:
one or more antibodies directed against the NKG2D receptor polypeptide in the chimeric NKG2D receptor and/or one or more antibodies directed against one or more of said NKG2D ligands; and/or
an antibody or small molecule that specifically binds to a Phosphoinositide 3-kinase (PI3K) polypeptide which inhibits PI3K signaling.

11. A method of treatment in a subject comprising a disease characterized by NKG2D expressing cells which are involved in the disease pathology comprising administering an effective amount of engineered immune cells according to claim 8.

12. The method of claim 11, wherein the disease comprises a cancer characterized by NKG2D expressing cancer cells.

13. A method of treating a subject comprising a disease characterized by NKG2D expressing cells which are involved in the disease pathology, comprising administering the composition of claim 10.

14. The method of claim 13, wherein the disease is a cancer, characterized by NKG2D expressing cancer cells.

15. The method of claim 11, wherein the immune cells comprise at least one of T cells, NK cells, NKT cells, stem cells and iPSCs.

16. The method of claim 12, wherein the immune cells comprise at least one of T cells, NK cells, NKT cells, stem cells and iPSCs.

17. The method of claim 13, wherein the immune cells comprise at least one of T cells, NK cells, NKT cells, stem cells and iPSCs.

18. The method of claim 14, wherein the immune cells comprise at least one of T cells, NK cells, NKT cells, stem cells and iPSCs.

* * * * *